US 6,704,497 B2

(12) United States Patent
Bikhovsky

(10) Patent No.: US 6,704,497 B2
(45) Date of Patent: *Mar. 9, 2004

(54) ELECTRIC HEATING DEVICES AND ELEMENTS

(75) Inventor: David Bikhovsky, Reut (IL)

(73) Assignee: Bar-Keser Project Management Initiatives and Economic consultants (1991) Ltd., Jerusalem (IL)

(*) Notice: Subject to any disclaimer, the term of this patent is extended or adjusted under 35 U.S.C. 154(b) by 0 days.

This patent is subject to a terminal disclaimer.

(21) Appl. No.: 10/122,147

(22) Filed: Apr. 15, 2002

(65) Prior Publication Data

US 2003/0016954 A1 Jan. 23, 2003

Related U.S. Application Data

(63) Continuation-in-part of application No. 09/571,793, filed on May 16, 2000, now Pat. No. 6,483,990, which is a continuation-in-part of application No. 09/029,172, filed as application No. PCT/IL96/00096 on Sep. 3, 1996, now abandoned.

(30) Foreign Application Priority Data

Sep. 7, 1995 (IL) ................................. 115198
Jun. 25, 1996 (IL) ................................. 118739

(51) Int. Cl.[7] ................................. F24H 1/18
(52) U.S. Cl. ....................... 392/458; 219/548
(58) Field of Search ................. 392/407, 432–435, 392/438, 439, 458; 219/544

(56) References Cited

U.S. PATENT DOCUMENTS

| | | |
|---|---|---|
| 2,600,486 A | 6/1952 | Cox |
| 2,712,591 A | 7/1955 | Rogell |
| 2,719,213 A | 9/1955 | Johnson |

(List continued on next page.)

FOREIGN PATENT DOCUMENTS

| | | |
|---|---|---|
| DE | 25 05 395 | 8/1976 |
| DE | 34 18 612 | 11/1984 |
| EP | 0 054 160 | 6/1982 |
| EP | 0 357 945 | 3/1990 |
| EP | 0 609 088 | 8/1994 |
| FR | 975038 | 2/1951 |
| GB | 1088543 | 10/1967 |
| WO | WO 87/04902 | 8/1987 |
| WO | WO 96/03013 | 2/1996 |

OTHER PUBLICATIONS

Japanese Patent Office, Patent Abstracts of Japan: Abstract of JP 01063288 A, Inventor: Satoshi, "Hot Air Heater of Flat Heating Element Type", Mar. 9, 1989.

Japanese Patent Office, Patent Abstracts of Japan: Abstract of JP 04264383 A, Inventor: Kazuomi, "Flat–Type Heating Element", Sep. 21, 1992.

Japanese Patent Office, Patent Abstracts of Japan: Abstract of JP 05258842 A, Inventor: Yoshiteru, "Planar Heating Element and Its Manufacture", Oct. 8, 1993.

*Primary Examiner*—Thor Campbell
(74) *Attorney, Agent, or Firm*—Browdy and Neimark, P.L.L.C.

(57) ABSTRACT

Heating device having a substantially flat heating element with specifically selected physical parameters is provided for heating an object to a required temperature. The physical parameters are selected such as to, at a given power and at a selected voltage supply to the heating element, provide as low as desired temperature gradient between the temperature of the outer surface of the heating element through which heat is dissipated and the required temperature of the object. Heating devices of the invention may be implemented in domestic heaters, in food cooking devices, in medical devices, etc. Also provided is a method for designing heating elements for use in such devices.

17 Claims, 15 Drawing Sheets

U.S. PATENT DOCUMENTS

| | | |
|---|---|---|
| 3,244,858 A | 4/1966 | Thorpe, Jr. |
| 3,525,850 A | 8/1970 | Hager, Jr. |
| 3,584,198 A | 6/1971 | Dol et al. |
| 3,737,624 A | 6/1973 | Eilenberger |
| 3,846,620 A | 11/1974 | Hocker |
| 3,892,947 A | 7/1975 | Strengholt |
| 4,015,105 A | 3/1977 | Dunn |
| 4,032,751 A | 6/1977 | Youtsey et al. |
| 4,203,198 A | 5/1980 | Hackett et al. |
| 4,551,614 A | 11/1985 | Johnson |
| 4,665,308 A | 5/1987 | Courvoisier et al. |
| 4,726,288 A | 2/1988 | Lansing |
| 4,801,782 A | 1/1989 | Ineson |
| 4,948,951 A | 8/1990 | Balzano |
| 5,035,561 A | 7/1991 | Loibl |
| 5,380,988 A | 1/1995 | Dyer |
| 5,440,425 A | 8/1995 | Kadooka et al. |
| 5,814,792 A | 9/1998 | Wildi |
| 6,483,990 B1 * | 11/2002 | Bikhovsky .................. 392/458 |

\* cited by examiner

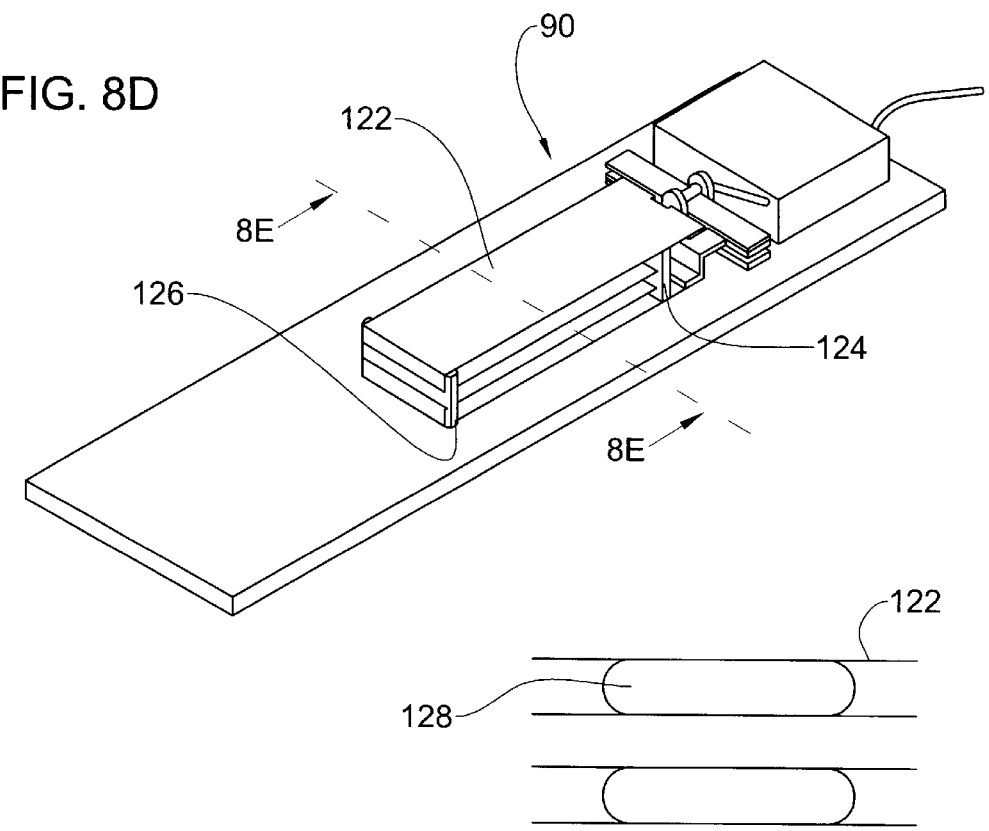
FIG. 8D
FIG. 8E
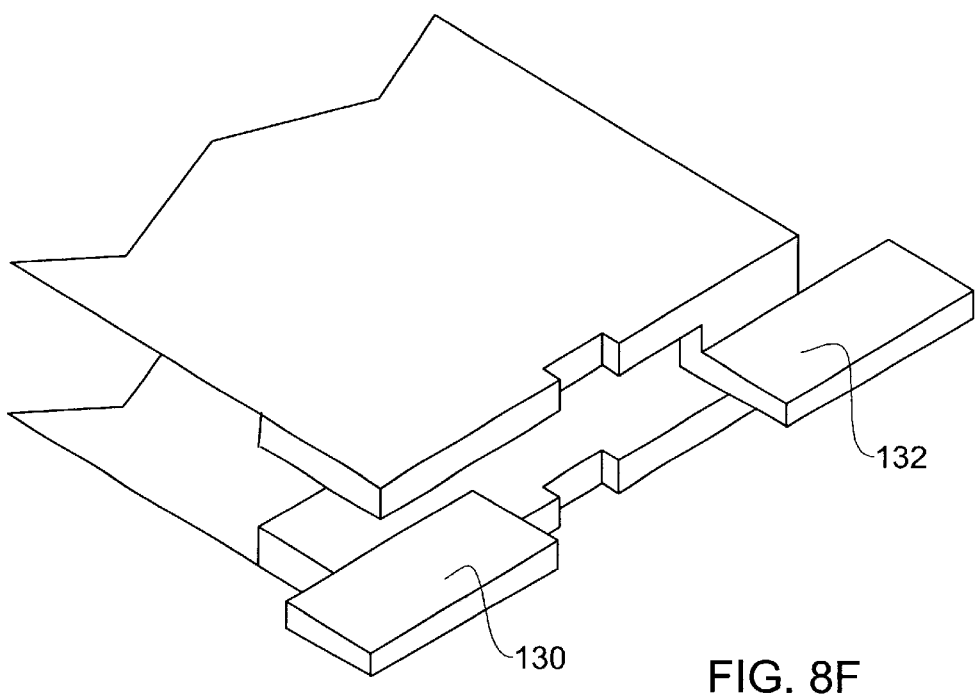
FIG. 8F

ELECTRIC HEATING DEVICES AND ELEMENTS

This is a continuation-in-part of parent application Ser. No. 09/571,793, filed May 16, 2000 now U.S. Pat. No. 6,483,990, itself a CIP of Ser. No. 09/029,172 (now abandoned) nationalized Apr. 17, 1998, as a National Phase of PCT/IL96/00096 filed Sep. 3, 1996.

FIELD OF THE INVENTION

The present invention relates to electric heating devices in general and in particular to heating elements useful in such devices.

BACKGROUND OF THE INVENTION

Heating devices employed for household, industrial or other use have typically a heating element which is embedded within the device and which then transfers heat by radiation, convection or conductance to an output surface of the device. The temperature at the output surface of the device is thus much lower than the working temperature of the heating element. There is usually a very big temperature drop between the temperature of the heating element which ranges from 100's to 1,000's° C., depending on the type of device, to a temperature at the output surface which may range from 60–90° C. for household heating devices to 120–300° C. for household cooling and baking devices.

Heating devices come in a large variety of form and shape. For example, one type of electric heating device has a bare heating element typically fashioned as either a band or a wire made from an alloy containing nickel and/or chromium and which typically reaches working temperatures ranging from about 400° C. to 1600° C. The heat generated by this type of heating elements is dissipated to the surrounding medium by mainly one or any combination of three heat transfer mechanisms, these be radiation natural or free convection or forced convection (e.g. by the use of a ventilator). Such heating devices enjoy the advantages of being inexpensive, small of a relatively low weight and having a long lifetime. However, they suffer from a drawback arising out of the high working temperature of their heating elements which poses a safety hazard.

In another type of electric heating device, commonly known as the electric radiator, the hazards associated with the bare heating element type of heating device are eliminated by submerging a heating element in a reservoir of oil or a similar liquid employed for transferring the heat generated by a heating element to the external walls of the radiator. Typically, the output temperature of a domestic heating radiator is about 70° C. whereas the working temperature of its heating element is 700° C. or above. Consequently, such a domestic heating radiator is typically equipped with heat-insulating means. As is well known, electric radiators suffer from the disadvantages that they are expensive, heavy, and relatively inefficient U.S. Pat. No. 2,600,486 discloses an electric heating element which comprises a flexible conducting metal sheet in which slits are cut so as to form an elongated relatively narrow tortuous flow path for an electric current. A similar kind of heating device is also disclosed in U.S. Pat. No. 3,584,198, U.S. Pat. Nos. 3,525,850 and 4,551,614 disclose an electric heater comprising elongated heating elements in the form of corrugated metallic ribbons which are heated to a temperature ranging from about 1200° F. to 1800° F. (about 650–1000° C.). U.S. Pat. No. 2,719,213 discloses a heating device in the form of a flat panel which comprises an electric conductor arranged in a plane between two different non-conducting sheets or layers, French Patent Specification 975,038 discloses a heating element in the form of arrogated plates Another heating panel is disclosed in U.S. Pat. No. 3,244,858 wherein an electric heating wire is arranged in a plane to track a zig-zag path over both sides of a non-conducting planar core. U.S. Pat. No. 4,203,198 discloses a planar heating device employing a heating element arranged in a plane to track a tortuous path and sandwiched between two sheets of fiber glass. Another heating device with a heating element arranged in a plane between two insulating sheets has been disclosed. U.S. Pat. No. 4,032,751 discloses a planar heating element utilizing electrically conducting carbonaccous pyropolymers. An electric planar heating device intended for use as an electrical bandage is described in U.S. Pat. No. 2,712,591, wherein an electrically conducting ribbon is described in U.S. Pat. No. 2,712,519, wherein an electrically conducting ribbon is embedded in a resilient strip of insulating material. A flexible circuit heater which can be used within clothing or the like is disclosed in U.S. Pat. No. 4,948,951, utilizing an electrically conductive strip made to track a tortuous path within a flat flexible member. U.S. Pat. No. 4,665,308 discloses an electrical heating element that can be incorporated in the lining of an item of clothing which makes use of a ductile insulated metal wire fixed to a metal sheet.

GENERAL DESCRIPTION OF THE INVENTION

There is accordingly a need in the art to provide an electric heating device for heating an object to a required temperature that eliminates the need for thermo-insulating means or at least substantially reduces the requirements to such means.

It is an object of the invention to provide a novel heating device with as low as desired temperature gradient between the temperature of the outer surface of a heating element and the required temperature of the heated body.

It is an object in accordance with some embodiments of the invention to provide a heating device wherein the heating element constitutes the heat dissipating, output surface of the device.

It is an object in accordance with some other embodiments of the invention to provide a heating device wherein the heating element is embedded in or forms a structural element of a household object serving also a purpose other than heating.

It is furthermore an object of the invention to provide domestic enclosure heating devices, electric cooking devices and therapeutic heating devices having characteristics in accordance with the above objects.

It is furthermore an object of the invention to provide a method for designing in constructing such heating devices.

Other objects of the invention will be clarified after reading the text below.

Generally speaking, the present invention provides a method and device capable of a so-called "low-gradient" heating. In practice, in most cases it is desired to have substantially low gradient between the surface temperature of a heating device and the temperature of the heating object, so as to reduce the danger of fire, as well as the danger of burns, when applying a heating device to the body for medical purposes. Additionally, such a low-gradient heating enables to reduce the requirements of electro- and thermo-insulation, and to increase the effectiveness of heating (i.e., achieving a desired effect at minimal energy). This means that in order to create a high-quality heating device, its heating element, intended for heating a given object, should be independently designed and calculated, taking into account not only the power required to obtain a desired temperature of the object but also the fact that the surface temperature of the heating element should be as low as desired different from the required temperature of the heated object. This is a very complicated task, since the transfer of heat from the heating element towards the object is proportional to the temperature gradient (i.e., to the difference between the temperature of the heating element and the temperature of the heated object). Accordingly, the desired decrease of the temperature gradient should be compensated, and practically, the single solution for this is a maximal increase in the surface area of the heating element.

Thus, the main idea of the present invention consists of designing a heating element whose surface temperature and surface area are independent selected at the given power required for heating a given object to a required temperature.

It was found by the inventor, that the solution for the above task is based on directionally varying the ratio between an electric current passing through the heating element and voltages at its input and output circuits. For the purpose of independent control of the surface temperature and surface area of the heating element, materials for the heating element should be selected in accordance with their physical parameters, namely, the specific resistivity and dimensions of the heating element, wherein the latter is in the form of a planar band having a substantially rectangular cross-section.

The inventor has found that in order to obtain the required effect, i.e., independent control of the surface temperature and surface area of the heating element at a given power, the width, b, and length, l, of the heating band should be selected so as to satisfy the following relations:

$$b \geq k \cdot I \cdot \sqrt{\frac{\rho}{\delta}}$$

$$l \geq k \cdot U \cdot \sqrt{\frac{\delta}{\rho}}$$

wherein I and U are the electric current (A) and voltage (V) of the heating element; $\rho$ is the specific resistivity (Ohm·mm$^2$/m); k is the so-called "correction coefficient" selected in accordance with the following two considerations: first, the value of k should be increased in those cases, when the surface area and the surface temperature of the heating element should be, respectively, increased and decreased; second, k should be of the same magnitude in the above equations, wherein the length units are meters, and the width and thickness units are millimeters.

The physical sense of the above equations will now be explained. The relationship between the heat power rating W of an electric heating element and its surface area S required to dissipate the heat generated thereby, can be approximated by the following equation:

$$S = k_1 W$$

Here, $k_1$ is the coefficient that depends on a variety of factors, including the surface temperature of the heating element, the medium surrounding the heating element (e.g., air, water or another fluid), the ambient temperature of the surrounding medium, and to a lesser degree, the location of the heating device within its local environment and the like.

As such, the values of $k_1$ can be obtained empirically by an artisan for various specific cases. For example, it is known an electric heating element having a surface temperature of about 70–90° C. requires about 0.7–0.8 m$^2$ surface area to dissipate 0.5 K watt in an environment having an ambient temperature of 20° C.

According to the invention, the heating element is a planar band having a length l along which the potential U falls, and a generally rectangular cross section having a width b and a thickness $\delta$. As such, the heating element has one or two major surfaces (as the case may) each having an area lb), through which heat is dissipated. The surface area S of the heating element can be approximated by the following equations:

$$S = k_2 bl$$

wherein $k_2$ is a coefficient which is approximately equal to 1 or to 2, depending on the number of surfaces through which heat is dissipated.

As is well known, the power rating W of an electric device, for example, an electric heater, is defined as the product of an operating potential U and an operating current I, i.e., W=IU. The operating potential U is equal to the product of the conductor's operating current I and electrical resistance R, i.e., U=IR. Further, the electrical resistance R of a conductor depends on the specific resistivity of an electrically conductive material from which the conductor is fabricated and the physical dimensions of the conductor, in accordance with the following equation: R=$\rho$l/A. Here, $\rho$ is the specific resistivity of the electrically conductive material, l is the length of are conductor, and A is the cross-sectional area of the conductor, i.e., A=b$\delta$.

Thus, from the above equations, we have:

$$W = I^2 R; \quad W = U^2/R$$

$$S = k_1 I^2 R; \quad S = k_1 U^2/R; \quad S = k_1 I^2 \rho l/b\delta; \quad S = k_1 U^2 b\delta/\rho l$$

Hence, $$k_2 bl = k_1 I^2 \rho l/b\delta; \quad k_2 bl = k_1 U^2 b\delta/\rho l$$

The length l and width b of the heating element can now be expressed as follows:

$$l = \sqrt{\frac{k_1}{k_2}} \cdot U \sqrt{\frac{\delta}{\rho}}$$

$$b = \sqrt{\frac{k_1}{k_2}} \cdot I \sqrt{\frac{\rho}{\delta}}.$$

It is thus understood that $k = (k_1/k_2)^{1/2}$.

To more clearly illustrate the essential features of the present invention, let us consider the following example of designing a heating element of a heating device intended for use in physiotherapy. Assume that the surface temperature of the heating element has to be in the range of 41–43° C. From experimental results, it appears that the coefficient k equal to 2 corresponds to this temperature value. A band of stainless steel with the thickness $\delta$ of 0.05 mm and specific resistivity $\rho$ of 0.7 Ohm·mm$^2$/m is selected as an electrically conductive material for fabricating the heating band. It is known that, in this specific application (i.e., physiotherapy), the power to be transferred to an object to be heated (i.e., a patient's body) is about 50 Watt. Let us consider two possible cases: (1) The selected voltage U is 10V, and consequently, the electric current I is 5A; and (2) the voltage U and current I are, respectively 5V and 10A.

Hence, for the first case, we have:

$$b_1 = 2 \cdot 5 \cdot \sqrt{\frac{0.7}{0.05}} \approx 37.4 \text{ mm} \quad l_1 = 2 \cdot 10 \cdot \sqrt{\frac{0.05}{0.7}} = 5.4 \text{ m}$$

The surface area $S_1$ of the heating element through which heat is dissipated is calculated as follows:

$$S = b_1 \cdot l_1 = 37.4 \text{ mn} \cdot 5.4 \text{ m} = 2 \cdot 10^5 \text{ mm}^2$$

For the second case we have:

$$b_2 = 2 \cdot 10 \cdot \sqrt{\frac{0.7}{0.05}} \approx 74.8 \text{ mm} \quad l_2 = 2 \cdot 5 \cdot \sqrt{\frac{0.05}{0.7}} \approx 2.7 \text{ m}$$

The surface area $S_2$ of the heating element through which heat is dissipated is calculated as follows:

$$S_2 = b_2 \cdot l_2 = 2 \cdot 10^5 \text{ mm}^2$$

It is thus evident that, the variation of the ratio between the electric current I and voltage U, with the given constant power and with the constant surface area of the heating element (i.e., with the fixed temperature), enables to control the geometry of the heating element, namely, to control the ratio between the length and width of the heating element.

If the temperature of the heating element has to be changed with the same power, it can be achieved by select an appropriate value of the coefficient k, keeping in mind that an increase in the value of k leads to an increase in the surface area S, and, consequently, leads to a decrease in the surface temperature of the heating element.

The ratio between the length and width of the heating element can be affected by the selection of an appropriate electrically conductive material. As follows from the above equations, under the fixed values of current and voltage, the higher the specific resistivity $\rho$ of the heating element and the lower its thickness $\delta$, the higher the length l of the heating element and the lower its width b.

Thus, the present invention allows for simultaneously and independently controlling the temperature and geometry of a heating element. This is a new approach, which has never been used for designing heating elements. According to this approach, initially, parameters defining the requirements of a specific application are set, namely, the power for heating a given object to a required temperature and the voltage to be supplied to the heating element, in accordance with a predetermined application of the heating device. It should be understood that these parameters, i.e. power and voltage, are defined independently. Then, the surface area of a heating element through which this power is to be dissipated is determined, and the physical parameters of the heating element (length, width, thickness and specific resistivity) are selected to meet the requirements of the specific application.

The present invention relates to domestic, industrial and other heating devices suitable for a wide range of applications including, but not limited to, heating enclosed spaces, heating food, therapeutic purposes and the like, and relates to electric heating elements for use therewith.

In the following, the term "heating device" will be used at times. This term should be construed in a broad manner mainly to relate to any device or object wherein one or its intended uses is heating. In accordance with the prior art, a heating device is typically a dedicated device designed for a single function, namely heating. However, in accordance with the invention, by some embodiments thereof, the heating device is embedded in or forms parts of objects having an entirely different purpose. For example, the heating element may form a structural component in a piece of furniture thus having a dual role in such an object. Thus, the term "heating device" should be understood, depending on the context, as referring also to such dual-role objects.

The present invention allows in fact to design heating elements for every purpose, need and in any desired form. This unique feature of the invention allows to incorporate the heating element as a structural element or as an add-on element in a large variety of objects, including various domestic constructional units (e.g. door frames) furniture, etc.

The heating element of the invention dissipates heat at practically any desired power rating, with a working temperature of the element which is way below the working temperature of the heating element of prior art devices operating with a comparable power rating. For example, in a heating device of the invention suited for domestic interior heating, the 4V heating element may be designed to operate with a working temperature of 70–80°, which is the conventional output temperature of heating devices, and accordingly, the heating element may be placed and form the external output surface of the heating device.

In order to avoid electric shock hazards, the heating element of the invention may be designed to operate under relatively low voltage, ranging, depending on the application, between 1V and 24V (which is the conventional upper limit in low voltage systems).

In accordance with the present invention, the heating element to suit a specific application is designed on the basis of novel developed relationships which allow to match the physical parameters of the heating element (dimensions and specific resistivity), to the electrical parameters of the heating element (desired voltage and power rating). These relations allow to choose the appropriate heating element to suit a specific application. Given the fact that the heating element operates at a relatively low temperature, it may be made from a wide variety of alloys, which cannot be used in conventional (prior art) heating devices, such as aluminum stainless steel, copper, etc.

According to the gene teaching of the invention, there is thus provided a heating device for heating an object to a required temperature, the heating device comprising a heating element and a power source for supplying voltage to the heating element, wherein:

the voltage U to be supplied to the heating element is selected in accordance with a predetermined application of the heating device.

the heating element is made of a selected electric conductive material of a specific resistivity $\rho$, is substantially flat and has a substantially rectangular cross section, so as to define at least one major outer surface through which a given heating power required for heating said object to said required temperature is dissipated, length l, width b and thickness $\delta$ of the heating element being selected such as to satisfy the following relations:

$$b \geq k \cdot I \cdot \sqrt{\frac{\rho}{\delta}}$$

$$l \geq k \cdot U \cdot \sqrt{\frac{\delta}{\rho}}$$

wherein I is the electric current passing through the heating element; $\rho$ is the specific resistivity (Ohm·mm²/m); δ is the thickness of the heating element in millimeters; k is a correction coefficient providing the units of length and width in meters and millimeters, respectively, and selected such that an increase in the value of k results in an increase in the surface area of the heating element and decrease in the surface temperature of the heating element;

the heating device thereby providing a desired temperature gradient between said at least one major surface of the heating element and said required temperature.

Where the electric heating device is employed to heat air at an initial ambient temperature of about 20° C. (room temperature) to a temperature of 100° C. or more or to heat a water based medium consisting of at least 50% water which is initially at room temperature, to a temperature up to about 50° C., k will preferably be within the range of 0.2–0.6.

In case the heating device of the invention is employed to heat air at room temperature to a temperature of up to about 90° C. or less, k will preferably be above 0.6.

The present invention allows to design a heating element to suit practically, any desired need. At times, the length and width of the elements are predetermined by the shape of the heating device, leaving a certain degree of freedom in the choice of alloy (and hence of the specific resistivity ρ) and thickness of the element is may be the case, for example, in heating devices in which the heating element is incorporated in another object, e.g.; a piece of furniture. In other cases, the material and hence the specific resistivity ρ is predetermined, leaving a degree of freedom for other physical parameters, being one of the length, width and thickness. This may be the case, for example, in heating devices where the heating element is intended to come into direct contact with a food item where the alloy from which the heating element is made will typically be stainless steel. These are only examples, but it is clear that it is possible, for practically all applications, to find, based on the above relations for length and width, a combination of parameters which allow to design an appropriate heating element namely, a bearing element which provides as low as desired temperature gradient between the outer surface of the heating element and the required temperature of the heated body.

By a specific aspect of the invention there is provided a heating device comprising a heating element incorporated as a structural element in a stationary object such as a piece of furniture, door or window frames, etc. In accordance with a further specific aspect of the invention, there is provided a heating device comprising a heating element embedded in or enclosed within such a stationary object.

Another specific aspect of the invention concerns a device for food heating. The term "food heating" should be understood as referring to one of a variety of heat-based food processing techniques including cooking, baking or grilling.

The novelty in the cooling device of the invention is in that it comprises a metal body which is either in contact with food or which is in proximity with food without any object between it and the food, said metal body serving as a heating element being thus connected to a power source for passing heating electric current therethrough.

In accordance with one embodiment of this latter aspect there is provided a cooking device for heating of liquid food, comprising a metal vessel for holding the food having metal walls serving as heating elements, and comprising a power source for passing low voltage, high electric current therethrough, thereby heating the liquid food contained therein. The electrical current parameter useful for such an application is typically voltage ranging from 1.0V to 12V with a power rating of 1–2KWatt.

In accordance with another embodiment of the latter aspect here is provided a device for heating solid food items, in which the solid food items are placed in direct contact with a metal plate, said metal plate serving also as a heating element and being connected to an electric power source for passing a heating electric current therethrough.

In accordance with yet another embodiment of the latter aspect, there is provided a device for heating food by means of heat irradiation onto the food, comprising a food-containing enclosure having one or more metal walls, at least one of said metal walls serving as a heating element to heat said enclosure and being connected to a power source for passing a heating electric current therethrough.

By a further aspect the present invention provides a heating device adapted to be worn or held on a body part for heating of that body part. By one embodiment of this aspect, such a device comprises a cloth or a cloth base matrix with a heating element embedded therein, the heating element having the above specifications. In accordance with another embodiment, the device comprises a liquid or gel-containing enclosure having pliable walls and con there a heating element being a heating element having the above characteristics.

By yet another aspect of the invention, there is provided a method for designing a substantially flat heating element having a substantially rectangular cross-section for implementing into a heating device for a predetermined application consisting of heating an object to a repaired temperature, the method comprising the steps of:

(a) defining a power rating W in accordance with the predetermined application;

(b) defining a range of operating potential U of the heating element in accordance with the predetermined application;

(c) selecting physical parameters of the heating element, so as to dissipate therethrough a heating power substantially equal to said power rating W, when the operating potential U falls onto the heating element, thereby providing a desired temperature gradient between the temperature of an outer surface of the heating element through which power is dissipated and said required temperature, wherein the selecting of the physical parameters comprises:

selecting an electrically conductive material with a specific resistivity ρ for fabricating therefrom said heating element and selecting dimensions of the heating element so as to satisfy the following relations:

$$b \geq k \cdot I \cdot \sqrt{\frac{\rho}{\delta}}$$

$$l \geq k \cdot U \cdot \sqrt{\frac{\delta}{\rho}}$$

wherein I is the electric current passing through the heating element; ρ is the specific resistivity (Ohm·mm²/m); l is the length of the heating element in meters; h is the width of the heating element in millimeters;

δ is the thickness of the heating element in millimeters; k is a correction coefficient providing the units of length and width meters and millimeters, respectively, and selected such that an increase in the value of k results in an increase in the surface area of the heating element and a decrease in the surface temperature of the heating element.

It will be appreciated that the actual working temperature in a heating device depends on a variety of factors, including the nature of the heating device environment, the exact geometry, etc., and therefore it is not always possible to predict the working temperature entirely on theoretical considerations.

Owing to the fact that the voltage to be supplied to the heating element is a varying parameter selected in accordance with a specific application, a step-down transformer should be used in a heating device according to the invention. However, at the frequencies of the existing power networks (i.e., 50 Hz and 60 Hz), the weight and dimensions of such a transformer are significantly high, which sometimes makes the use of the transformer inefficient. The development of modern inverters practically allows for eliminating weight and dimensions related problem, since the weight and dimensions of a transformer are in inverse proportion to the working frequency thereof.

The heating band according to the invention, due to its task, occupies a significantly large area, and consequently the induction C of its electric circuit will be significantly high. On the one hand, since the inductive resistance, $R_c$, is proportional to the frequency f (Rc=kf), this problem must be overcome. On the other hand, due to the substantially large area and relatively high electric currents (as compared to those flowing in conventional heating devices), the heating band may behave like an antenna that produces an electro-magnetic field presenting noise for electronic equipment in its vicinity.

The present invention also provides the solution for the above problem. This is implemented by accommodating wires connecting the heating band to a power source in the following manner. One of the wires is connected directly to one of the outputs of the heating band. The other wire, on its way to the other output of the heating band, passes along the entire circuit of the band so as to be substantially symmetrical to the band along its longitudinal axis. This enables to sharply reduce both the inductive resistance and the electromagnetic field.

Another problem arises when the condition, for obtaining low-gradient heating is associated with the need to work with substantially high electric currents, and consequently, substantially low voltages. Hence, the wire connecting the power source to the heating element has to be made with a substantially high cross section, which may affect the flexibility of the wire and thus may be undesirable in some applications (e.g., physiotherapy). This problem can be solved in the following manner. Since the weight and dimensions of a transformer operating with high frequencies are significantly low, an output transformer can be taken out of the inverter and mounted in a heating element. As a result a substantially low electric current flows through the wires connecting the power source to the heating element, thereby providing desired flexibility of the electrically conductive wires.

The case may be such that the supply of 220V or 110V to the heating element is undesirable for industrial safety provisions. In this case, an intermediate transformer reducing the voltage to 12V will function inside the inverter, while a transformer reducing the voltage to 1V and less will function inside the heating element. By this, the problem associated wilt the need to operate with substantially high currents, and consequently, relatively low voltages, can be solved.

BRIEF DESCRIPTION OF THE DRAWINGS

For a better understanding of the present invention and to show how the same may be carried out in practice, and solely by way of example, reference will now be made to specific embodiments with occasional reference to the accompanying drawings, in which:

FIGS. 8A to 8D show examples of a food heating system in accordance with another embodiment of the invention comprising an interchangeable heating element construction for use in a variety of food heating applications, wherein.

FIG. 8A shows a system with a heating element intended for baking heating of frozen food, etc. contained in the enclosure under the heating element;

FIG. 8B shows a cross-section along lines 8B—8B in FIG. 8A;

FIG. 8C is a cross-section through lines 8C—8C in FIG. 8A;

FIG. 8D shows the same system with a heating element intended for frying meat or the like;

FIG. 8E shows a cross-section through lines 8E—8E, in. FIG. 8D; and

FIG. 8F shows the attachment end of the heating element in FIG. 8 which attaches to the power supply outlet member;

FIGS. 9A and 9B show a therapeutic heating device in accordance with the invention, wherein FIG. 9A is a perspective view of a therapeutic heating device;

FIG. 9B shows the device of FIG. 9A in use while heating a portion of an individual's arm.;

FIGS. 10A and 10B show another embodiment of a therapeutic heating device, wherein FIG. 10A is a planar view of-the device;

FIG. 10B shows a device of FIG. 10A attached to an individual's leg;

FIGS. 12A and 12B show a therapeutic device for heating an individual's lower back, wherein FIG. 12A is a perspective view of the device;

FIG. 12B shows the device in use;

DETAILED DESCRIPTION OF THE EMBODIMENTS OF THE INVENTION

Figure 1:
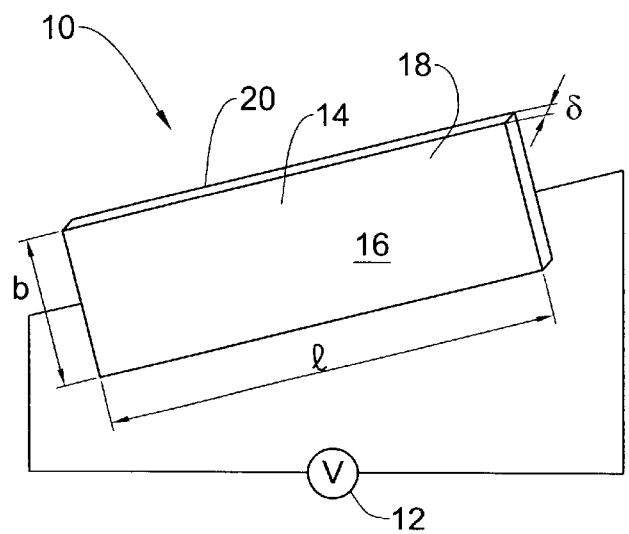
FIG. 1 is a schematic view of an electric heating device constructed and operative according to the teachings of the present invention.

With reference now to the drawings, FIG. 1 shows an electric heating device, generally designated 10 connected to a source of electric energy 12 implemented as any one of a wide range of conventional DC and/or AC sources. Hence, the source of electric energy 12 can be implemented as a mains supply, a battery, a down-step transformer, and the like depending, inter alia, on the environment in which the electric heating device 10 is deployed.

In its simplest form, the electric heating device 10 is implemented as an electrically conductive heating element 14 fashioned as a relatively thin, generally rectangular cross sectioned, plate or band 16 having a length l, breadth b and a thickness δ, so as to define front and back major surfaces 18 and 20, and side surfaces. In the case that the electric heating device 10 is free standing, the surface area S available to dissipate heat can be approximated as the combined surface area of the major surfaces 18 and 20. The combined surface area of the side surfaces is insignificant, as compared to that formed by the major sources.

The heating device 10 works under electric potential U and dissipates power at power ting W. The relationship between these parameters is in accordance with the above relations for length and width.

The heating element 14 is preferably prepared from materials which possess the following properties: relatively high conductivity, relatively low specific weight, high availability, a capability of being rolled in a rolling process to relatively thin, thicknesses of between about 0.01 mm to about 0.2 mm and the like. In case, where the element should serve as a structural element of an object, it may be desired that the material will have the needed strength for the additional fraction of the featured element. It is a particular feature of the invention that a wide range of materials which can be suitably employed as heating element 14 include, but are no limited to, steel with a specific resistivity ρ of between about 0.1 to about 0.13 Ohm-mm$^2$/m; spring steel with a specific resistivity ρ of between about 0.24 to about 0.4 Ohm-mm$^2$/m; transformer steel with a specific resistivity ρ of between about 0.5 to about 0.65 Ohm-mm$^2$/m; stainless steel with a specific resistivity ρ of between about 0.7 to about 0.8 Ohm-mm$^2$/m; copper based alloys with a specific resistivity ρ of between about 0.017 to about 0.025 Ohm-mm$^2$/m; gold with a specific resistivity ρ of between about 0.02 to about 0.03 Ohm-mm$^2$/m; titanium with a specific resistivity ρ of between about 0.4 to about 0.6 Ohm-mm$^2$/m; aluminum with a specific resistivity of between about 0.035 to about 0.05 Ohm-mm$^2$/m; and others. It should be noted that the specific resistivity of some alloys, such as aluminum, changes considerably with a change in temperature, and thus should be considered when designing the element.

Following are some examples of physical dimensions (thickness—δ, length—l, width—b, and weight—G (in grams)) of heating elements in accordance with the present invention for an electric heating device operating under different electrical conditions.

The following Tables I–IV, show examples of physical dimensions (thickness—δ, length—l, width—b, and weight—G (in grams)) of heating elements in accordance with the present invention for an electric heating device operating under a voltage of 220V for dissipating a power rating of 1 Kw for heating an air based medium at an ambient temperature of about 20° C., while maintaining a surface temperature of the heating element of about 70–80° C. Table I shows some examples of physical dimensions where the heating element is fashioned from carbon steel having a specific resistance of 0.13 Ohm-mm$^2$/m; Table II shows examples where a heating element is fashioned from spring, steel with a specific resistance of 0.40 Ohm-mm$^2$/m; Table III shows examples where a heating element is fashioned from a transformer steel with a specific resistance of 0.6 Ohm-mm$^2$/m; and Table IV shows examples where a heating element is fashioned from aluminum with specific resistance of 0.0270 Ohm-mm$^2$/m.

TABLE I

| δ(mm) | l(m) | b(mm) | G(g) |
|---|---|---|---|
| 0.015 | 52 | 9.1 | 56.7 |
| 0.038 | 73 | 6.5 | 113 |
| 0.05 | 95 | 5.0 | 190 |
| 0.10 | 133 | 3.8 | 404 |
| 0.20 | 185 | 2.7 | 799 |

TABLE II

| δ(mm) | l(m) | b(mm) | G(g) |
|---|---|---|---|
| 0.015 | 29.6 | 16.4 | 58 |
| 0.030 | 41.5 | 11.7 | 116 |
| 0.05 | 54.0 | 9.0 | 194 |
| 0.10 | 76.0 | 6.6 | 400 |
| 0.20 | 106 | 4.7 | 797 |

TABLE III

| δ(mm) | l(m) | b(mm) | G(g) |
|---|---|---|---|
| 0.015 | 24.7 | 20 | 59 |
| 0.030 | 34.6 | 14.3 | 118 |
| 0.05 | 45.0 | 11 | 148 |
| 0.10 | 63.0 | 8 | 400 |
| 0.20 | 88.0 | 5.7 | 800 |
| 0.40 | 124 | 4.0 | 1600 |
| 1.0 | 202 | 2.5 | 4040 |

TABLE IV

| δ(mm) | l(m) | b(mm) | G(g) |
|---|---|---|---|
| 0.015 | 99 | 4.8 | 19.0 |
| 0.030 | 140 | 3.5 | 39.7 |
| 0.050 | 194 | 2.5 | 65.0 |
| 0.10 | 273 | 1.9 | 132 |
| 0.20 | 385 | 1.3 | 270 |

Tables V and VI show examples of physical dimensions of heating elements in accordance with the present invention operating under a low potential of 12V for dissipating a power rating of 1 KWatt for heating an air based medium at an ambient temperature of about 20° C. while maintaining a surface temperature of about 70–80° C. Table V gives some physical dimensions in the case of transformer steel with a specific resistance 0.6 Ohm-mm$^2$/m and Table VI shows examples of physical dimensions for aluminum with a specific resistance of 0.0350 Ohm-mm$^2$/m. Both are for temperatures within the range of 70–80° C.

TABLE V

| δ(mm) | l(m) | b(mm) | G(g) |
|---|---|---|---|
| 0.015 | 1.33 | 370 | 59 |
| 0.030 | 1.87 | 262 | 117 |
| 0.050 | 2.4 | 201 | 192 |
| 0.10 | 3.4 | 142 | 386 |
| 0.20 | 4.8 | 100.7 | 773 |

TABLE VI

| δ(mm) | l(m) | b(mm) | G(g) |
|---|---|---|---|
| 0,015 | 5.5 | 89 | 20.0 |
| 0.030 | 7.75 | 63 | 39.5 |
| 0.050 | 10.1 | 48 | 65.0 |
| 0.10 | 14.2 | 34 | 130 |
| 0.20 | 20.0 | 24 | 259 |

Further features of electric heating devices in accordance with the teachings of the present invention as will become apparent hereinbelow are as follows: First, the surface temperature of the electric heating devices is generally low depending on the particular application at hand, thereby considerably lowering and at times totally eliminating the risks of burns, fires, and the like. Second, the current passing through the electric heating devices is generally quite high, but is not a potential source of electric shocks which occur due to high voltage and not high current. Third, low operating voltages can be used to energize the electric heating devices, thereby obviating the need for grounding, insulation, and the like. And lastly, the weight of the electric heating devices is generally quite low and, as evident in the above Tables, typically below 1 Kg.

Figure 2:
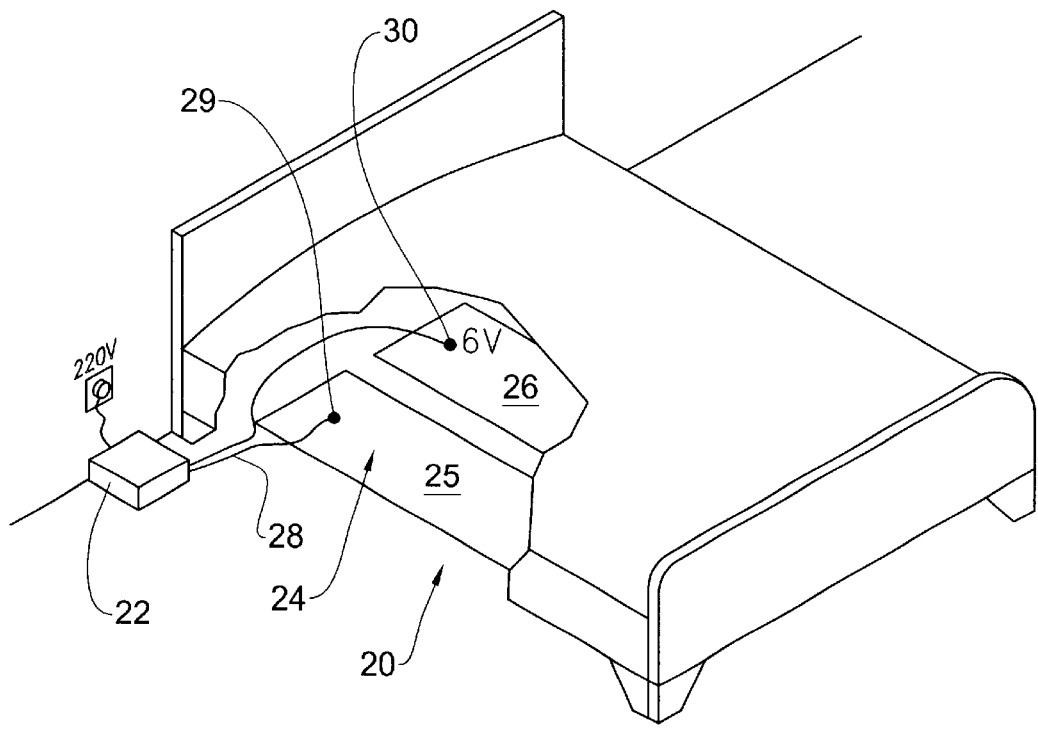
FIG. 2 is a perspective view of an electric heating device for providing a warm airflow around a bed.

Turning now to FIG. 2, an electric heating device is depicted, generally designated 20, for providing a comfortable heated air convection around a bed. The specifications of the electric heating device 20 may include, for example, a power rating of about 1 KWatt and an operating voltage of about 6V delivered by a step-down transformer 22 from a 220V AC mains supply.

In this case, the electric heating device 20 may, for example, be implemented as a heating element 24 made of transformer steel bands 25 and 26 having a specific resistivity ρ of about 0.6 Ohm-mm$^2$/m, a length l of about 1.7 m, a width b of about 280 mm and a thickness δ of about 0.05 mm. The electric circuit is formed by leads 28 connected one to each of bands 25 and 26 through contacts 29 and 30, respectively, and a shorting lead or band connecting the two bands 25 and 26 at their rear end (the latter not shown). The current flowing through the bands is about 165 Amps, and although leads 28 are represented here as thin leads and the contacts 29 and 30 are shown as point contacts, it will be appreciated that given the magnitude of the current, heavy leads and very low resistance contact have to be provided. Typically, surface temperature of the bands 25 and 26 is about 70–80° C. It should be noted that in accordance with the above relations for length and width, the values obtained for the length l and width b are: l≧1 m and b≧170 mm.

Figure 3:
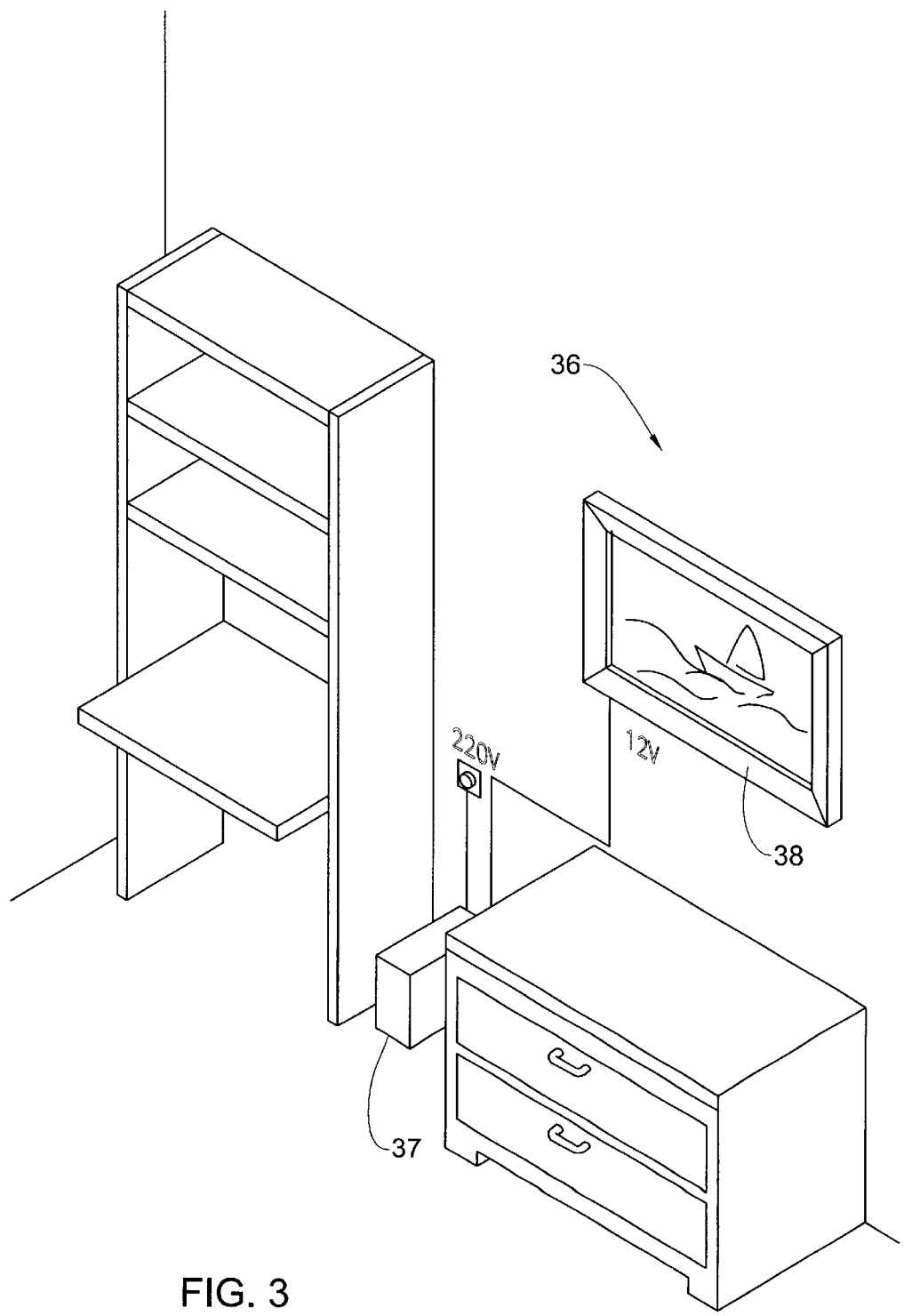
FIG. 3 is a perspective view of an electric heating device for heating a children's bedroom.

FIG. 3 depicts an electric heating device, generally designated 36, for heating a children's bedroom. The specifications of the electric heating device 36 may include a power rating of about 1 KWatt and an operating voltage of about 6V delivered by a step-down transformer 37 from a 220V AC mains supply.

In this case, the electric heating device 36 includes a heating element, implemented in a picture 38. The heating element (not shown) may have the form of an aluminum band having a specific resistivity ρ of about 0.035 Ohm-mm$^2$/m, a length l of about 5.0 m, a width b of about 80 mm, and a thickness δ of about 0.015 mm. The band can be provided as an array of continuously connected horizontal segments or continuously connected vertical segments forming a rectangular waveform like shape and the like. Typically, the surface temperature of the electric heating device 36 is in the range of about 50–60° C. It should be noted that in accordance with the above relations, the values obtained for the length l and width b are: l≧5 m and b≧70 mm. Picture 38 can be hung on a wall. In practice, the band is preferably insulated such as by being sandwiched between two polyethylene films and mounted on an aluminum sheet having a wooden or plastic frame.

Figure 4:
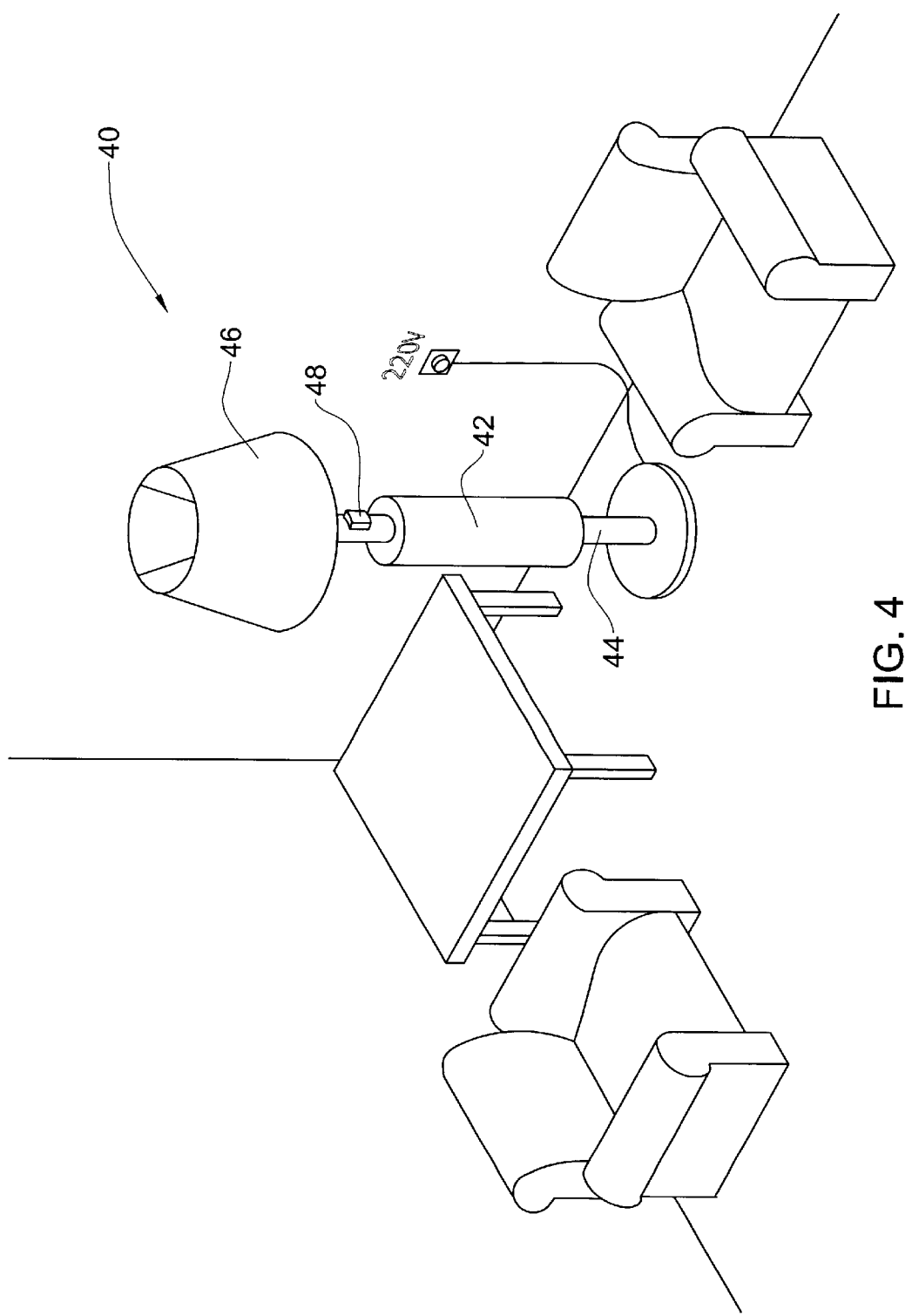
FIG. 4 is a perspective view of an electric heating device for heating a lounge.

FIG. 4 depicts an electric heating device, generally designated 40, for heating a lounge. This heating device is implemented as a cylindrical element 42 on a pole 44 of a free standing lamp 46. The specifications of the electric heating device 40 may include, for example, a power rating of about 1 KWatt and an operating voltage from a 220V AC mains supply.

In this example, the electric heating device 40 includes a heating element in the form of a transformer steel band which is enclosed within cylindrical heating device 42, having a specific resistivity ρ of about 0.6 Ohm-mm$^2$/m, a length l of about 0.38 m, a width b of about 10 mm and a thickness δ of about 0.05 mm. Typically, the surface temperature of the electric heating device 40 is in the range of about 70–80° C. It should be noted that in accordance with the above relations, the values obtained for the length l and width b are: l≧37.7 m. and b≧9.4 mm.

Device 40 is provided also with a three way switch 48 enabling operation of the electric heating device 42, the lamp 46, or both.

Figure 5:
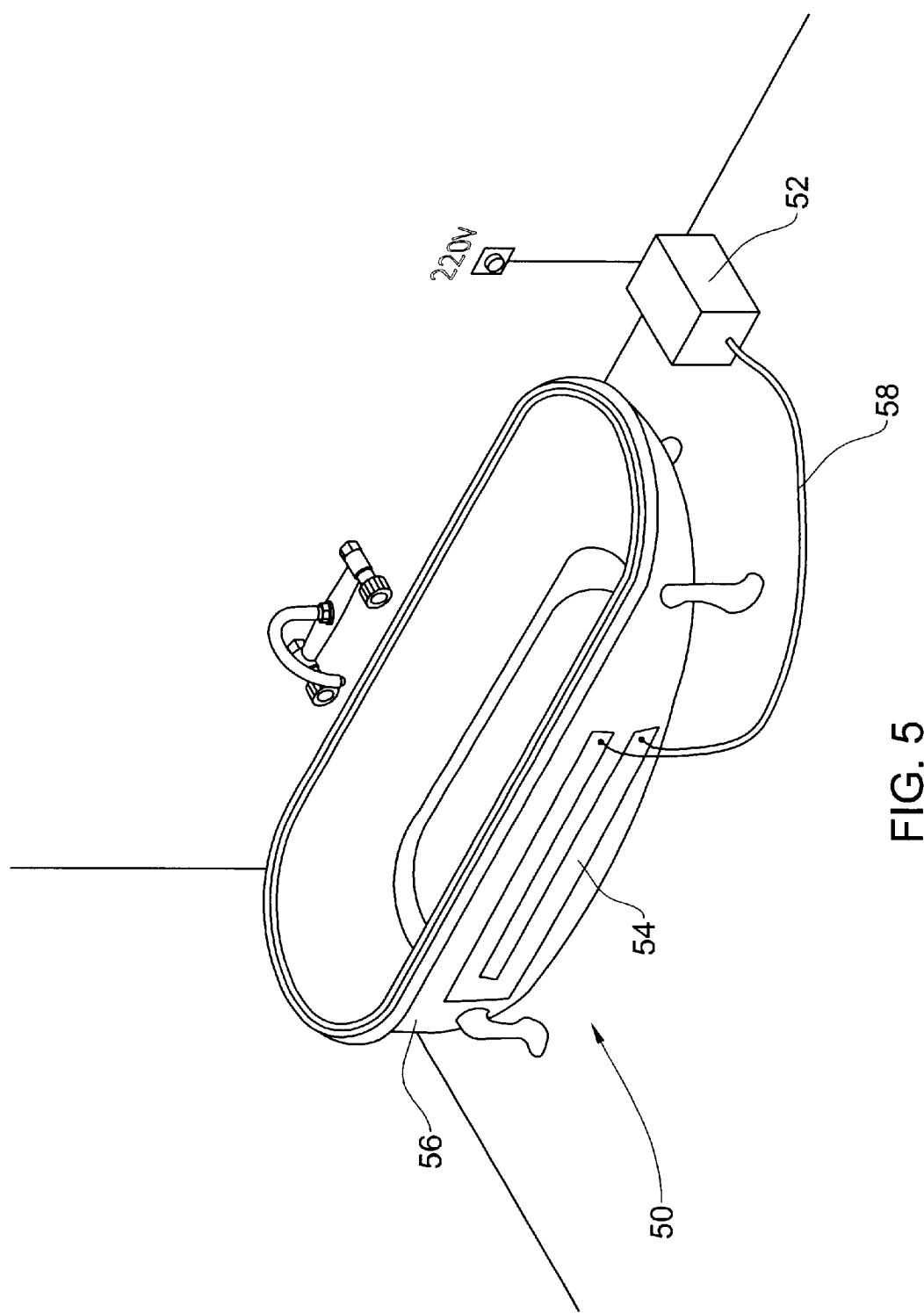
FIG. 5 is a view of a fragment of a domestic heating device wherein a heating element is embedded in a construction element such as a door frame.

FIG. 5 depicts an electric heating device, generally designated 50, for heating a bathroom. The specification of the electric heating device 50 may, for example, include a power rating of about 1.5 KWatt and an operating voltage of about 12V, obtained through a step down transformer 52 from a 220V AC mains supply. As shown, the electric heating device 50 comprises a heating element 54, formed from a band which tracks three sides of a right angled rectangle, which is attached, e.g., by gluing, to the outside surface of a bath 56. Element 54 is preferably covered by a water impermeable film, such as a polyethylene film. An electric current from transformer 52 is provided by leads 58 and similarly as in the embodiment shown in FIG. 2, the leads should be adapted to transfer the needed current (about 125 Amps) and the contacts of the leads with element 54 should be of a very low resistance.

The heating element 54 may, for example, be a stainless steel band having a specific resistivity ρ of about 0.75 Ohm-mm$^2$/m, a total length l of abut 2.5 m, a width b of about 200 mm and a thickness δ of about 0.1 mm. Typically, the surface temperature of the electric heating element 54 is about 60–80° C. It should be noted that in accordance with the above relations, the values obtained for the length l and width b are: l≧2.5 m and b≧200 mm.

Figure 6A:
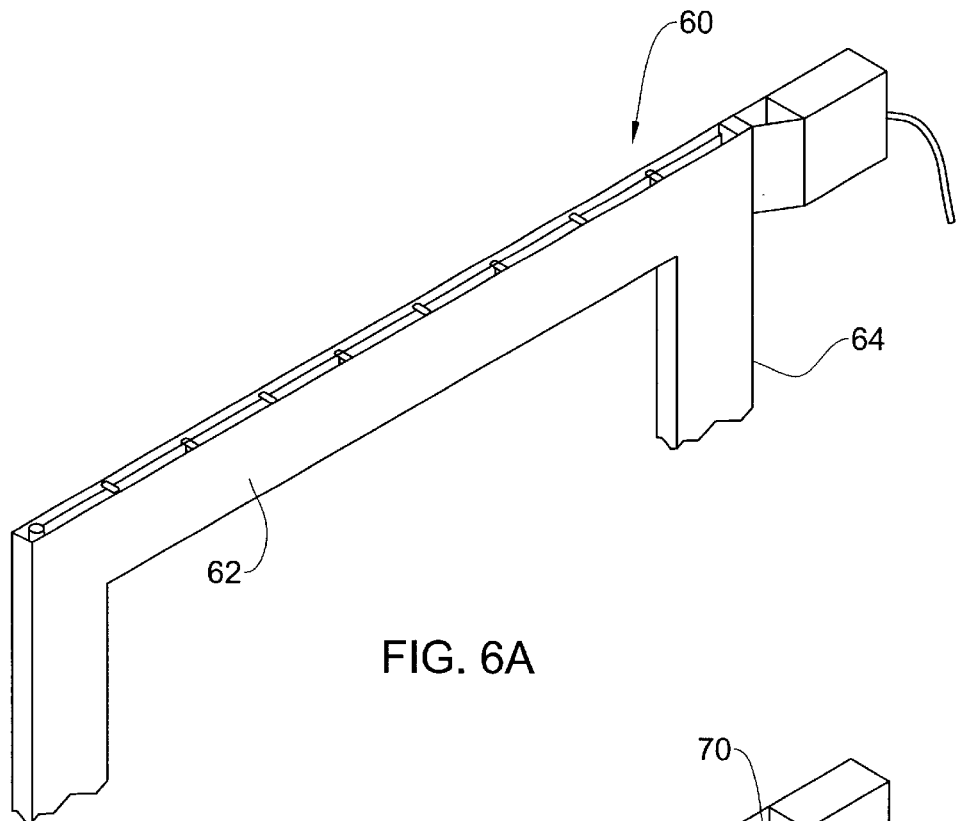
FIG. 6A is a perspective view of such an element.
Figure 6B:
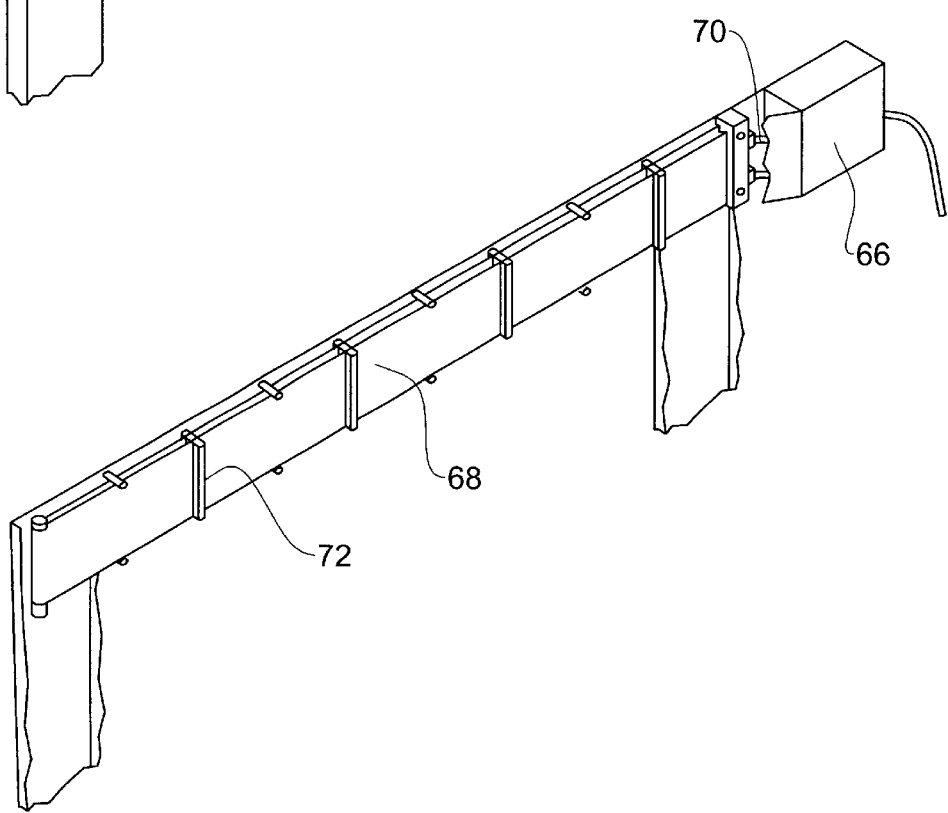
FIG. 6B shows the same element with the front wall removed to show the heating element.

FIGS. 6A and 6B show a heating device, generally designated 60, implemented within the upper beam 62 of a window or door frame 64. Heating device 60, as can particularly be seen in FIG. 6B, includes a step down transformer 66, receiving 220V AC mains supply, a heating element 68 in the form of a band which tracks a reciprocating path along the length of beam 62. An electric current to heating element 68 is provided through electric leads 70. The heating element 68 is provided with a number of space retainers 72 made from an insulating material such as heat resistant plastic or a ceramic.

Heating element 68, may for example, be a low alloy stainless steel band having a specific resistivity $\rho$ of about 0.3 Ohm-mm$^2$/m, a total length l of about 1.5 m (i.e. 2×0.75 m), a width b of about 100 mm and a thickness 67 of about 0.2 mm. The power rating is for example about 1 kW and the operating voltage is about 6V. During operation the heating element reaches a working temperature of about 70–80° C., and a temperature on the external surface of beam 62 will thus be about 35° C.

Figure 7:
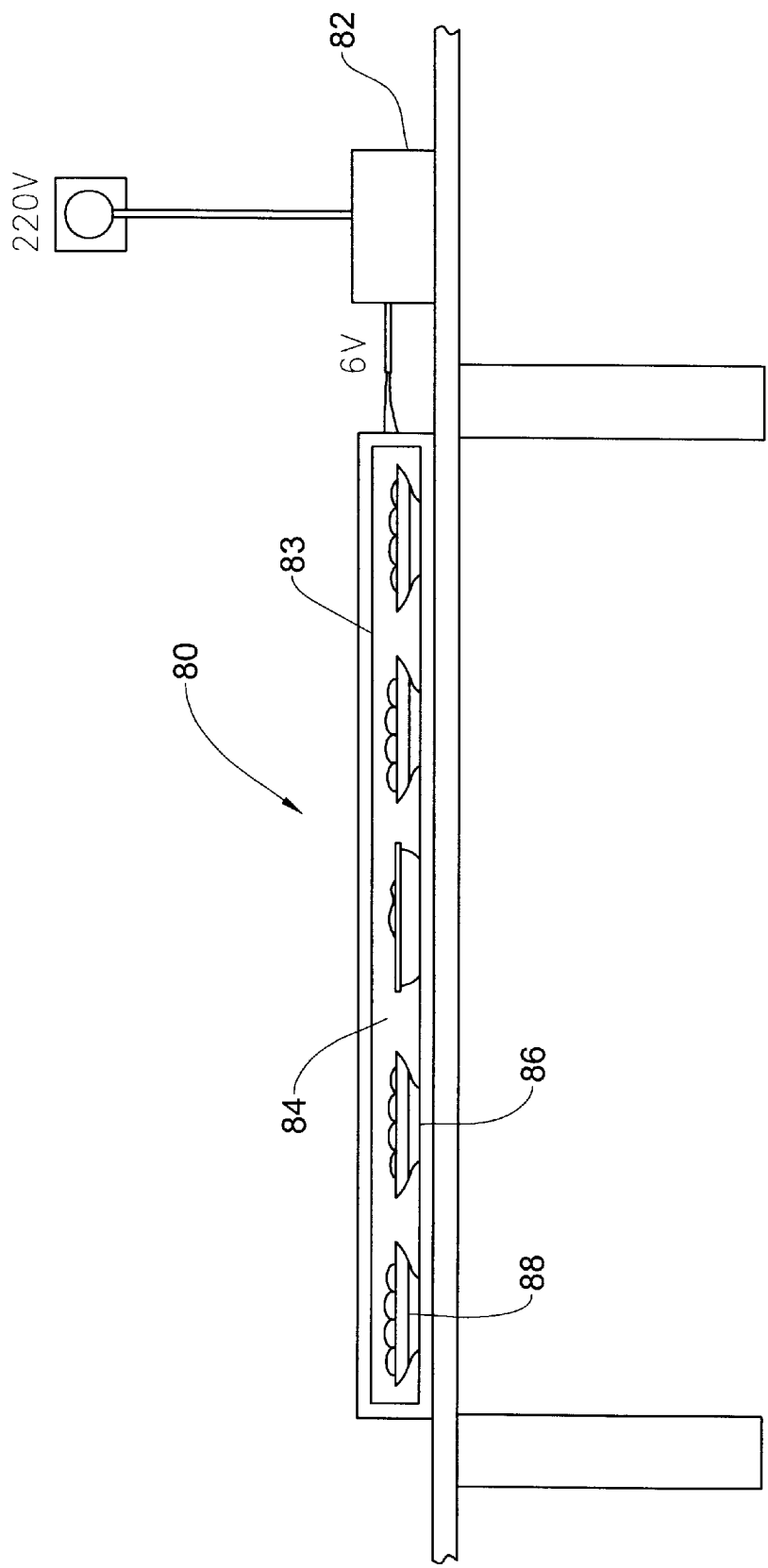
FIG. 7 is a perspective view of an electric heating device for heating food.

FIG. 7 depicts an electric heating device, generally designated 80, for heating food portions. The specifications of the electric heating device 80 include a power rating of about 1 KWatt and an operating voltage of about 6V obtained via a step down transformer 82 from a 220V AC mains supply.

In this case, the electric heating device 80 includes a heating element in the form of a stainless steel band having a specific resistivity $\rho$ of about 0.75 Ohm-mm$^2$/m, a length l of about 0.8 m, a width h of about 90 mm and a thickness $\delta$ of about 0.2 mm. Typically, the surface temperature of the electric heating element 80 is in the range of about 140–160° C. It should be noted that in accordance with the above relations for length and width, the values obtained for the length l and width b are: $l \geq 0.63$ m. and $b \geq 63$ mm. As shown, the electric heating element of device 80 is best included as the top surface 83 of the oven type device 84 with the bottom wall 86 made of an electrically non-conductive material. The heating of top surface 82 heats the enclosed volume including the one or more food portions 88.

Figure 8A:
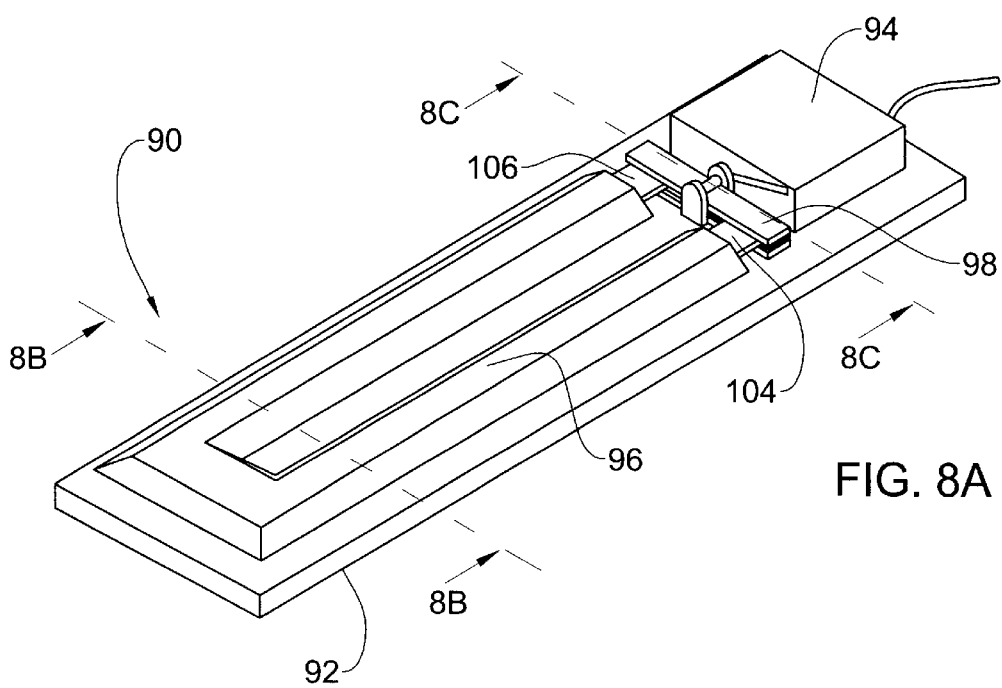
Figure 8B:
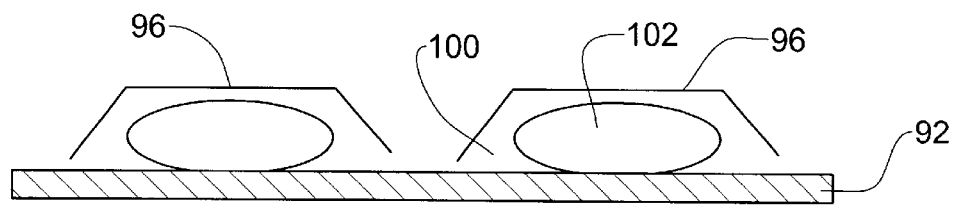
Figure 8C:
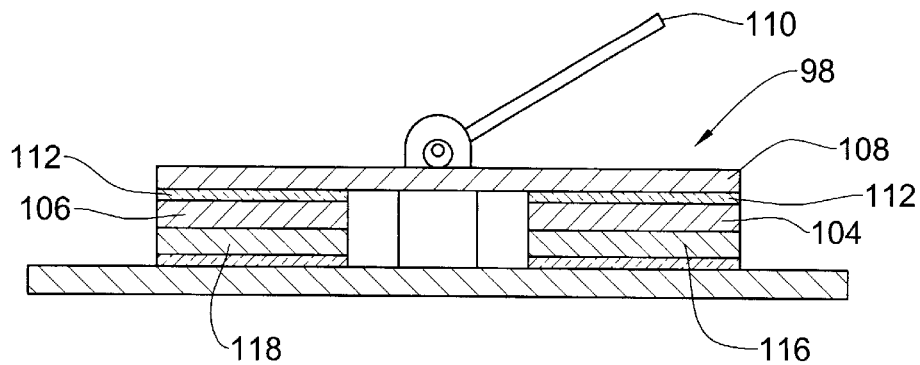

FIGS. 8A–8C show a cooking assembly with interchangeable heating elements for a variety of cooking applications. Assembly 90, shown in FIG. 8A, comprises a plate 92 made from an electrically insulating material, a step down transformer 94, a heating element 96 and an electric contact assembly 98. In the embodiment shown, cooking element 96 has a trapezoidal cross-sectional shape with the bottom side removed, as can best be seen in FIG. 8B. As can further be seen, heating element 96 defines an enclosure 100 containing food items 102, specifically food items to be baked.

The specifications of this heating device may include a power rating of about 1 kW and an operational voltage of about 3V. Element 96 is typically made of stainless steel having a specific resistivity $\rho$ of about 0.75 Ohm-mm$^2$/m having a total length (from one end to the other end of the looped path tracked thereby) of about 3 cm, a width (including two sides and upper walls of the element) of about 130 mm and a thickness of about 0.2 mm. During operation, the element has an output temperature of about 60–250° C. which heats up space 100 and brings to cooking of food items 102.

Contact assembly 98 which is shown in cross-section in FIG. 8C allows tight electric contact on the one hand and interchangeability on the other hand. Element 96 has two contact plates 104 and 106. Contact assembly 98 comprises a clamping plate 108 which is pushed downwards by means of a clamping lever 110 which by the intermediary of insulator sheet 112 clamps plates 104 and 106 to plates 116 and 118, respectively, which are electrically connected to the output of transformer 94.

FIGS. 8D–8F show system 90 incorporating a different heating element assembly 120. Assembly 120 comprises a heating element 122 fashioned as a band reciprocating between two members 124 and 126 made from an insulating material. Element 122 may typically be made of stainless steel with a specific resistivity of $\rho$ of about 0.75 Ohm-mm$^2$/m a total length l of about 0.6 m, a width b of about 80 mm and a thickness $\delta$ of about 0.2 mm.

The specification of this element includes a power rating of about 0.5 kW.

The working temperature achieved in this element is typically about 260° C. and suitable for frying food items such as, for example, meat. As can be seen in the cross-sectional view shown in FIG. 8E, food items 128 which may for example be steaks placed within different turns of element 122, may then be fired simultaneously from both sides.

FIG. 8F shows the electric contact members of element 126 including two metal plates 130 and 132 integral with the upper and the lower turn of the element, respectively. Generally, the power, and hence the temperature of the heating element of assembly 90 may be controlled by control means (not shown) adapted to change the output voltage.

Figure 9A:
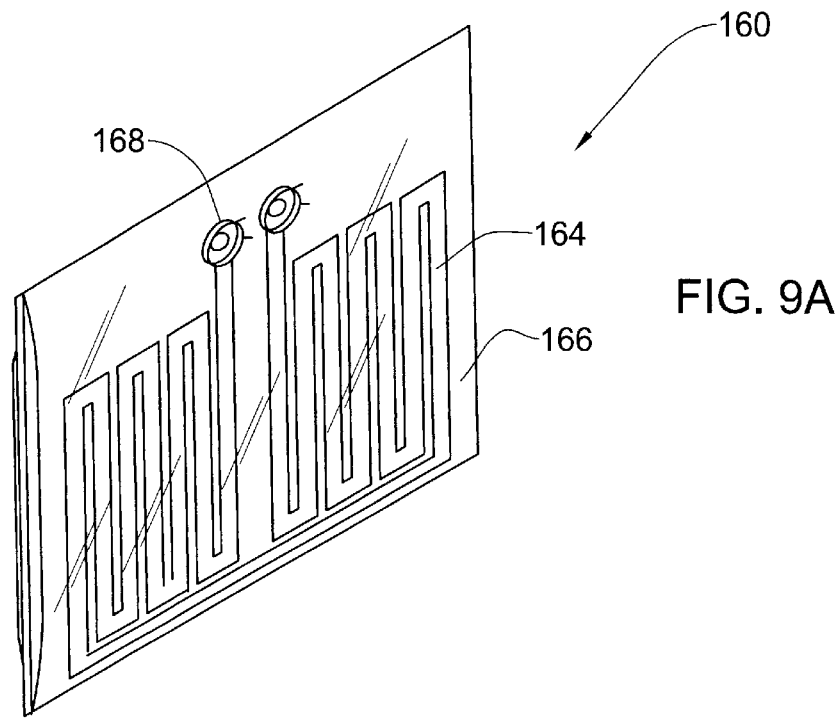
Figure 9B:
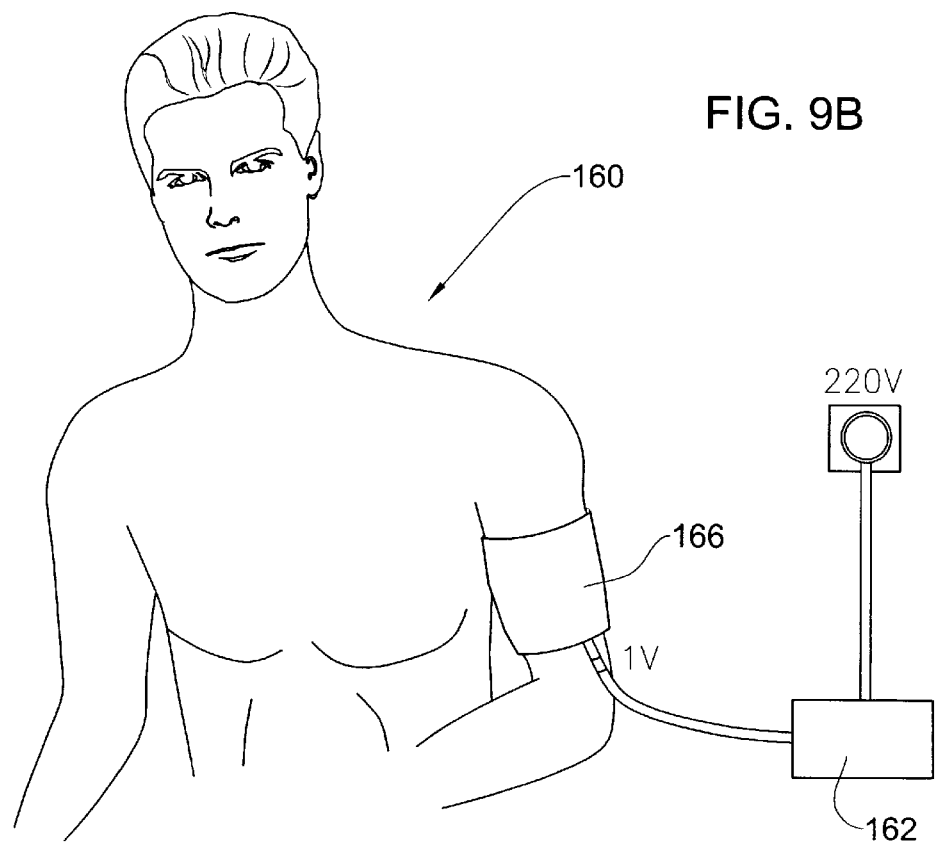

FIGS. 9A and 9B depict an electric heating device, generally designated 160, for therapeutic heating purposes. The specifications of the electric heating device 160 typically includes a power rating of about 100W and an operating voltage of about 6V achieved via a step down, transformer 162 from a 220V AC mains supply.

Device 160 includes a heating element 164 packaged within a plastic envelope 166 together with a quantity of a water-based gel and having ends connected to external sockets 168. The element has the form of a band, e.g. made of copper, having a specific resistivity $\rho$ of about 0.022 Ohm-mm$^2$/m, a length l of about 0.6 m, a width b of about 11 mm and a thickness $\delta$ of about 0.015 mm. It should be noted that in accordance with the above relations, the values obtained for the length l and width b are: $l \geq 0.5$ m and $b \geq 7$ mm. Typically, the surface temperature of the envelope 166 is about 40–45° C. As can be seen in FIG. 9B, the device may be attached to an arm or to another body part as needed, for heating of the arm or the other body part. The attachment may be by rubber strings, bands, etc., as generally known per se (not shown in FIG. 9A).

Figure 10A:
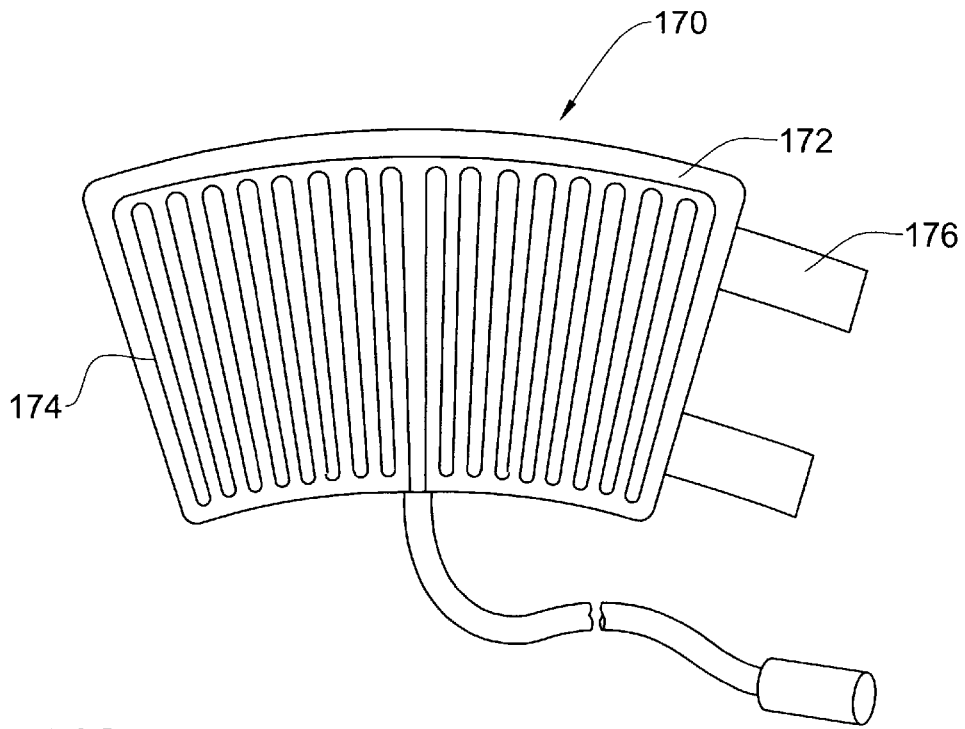
Figure 10B:
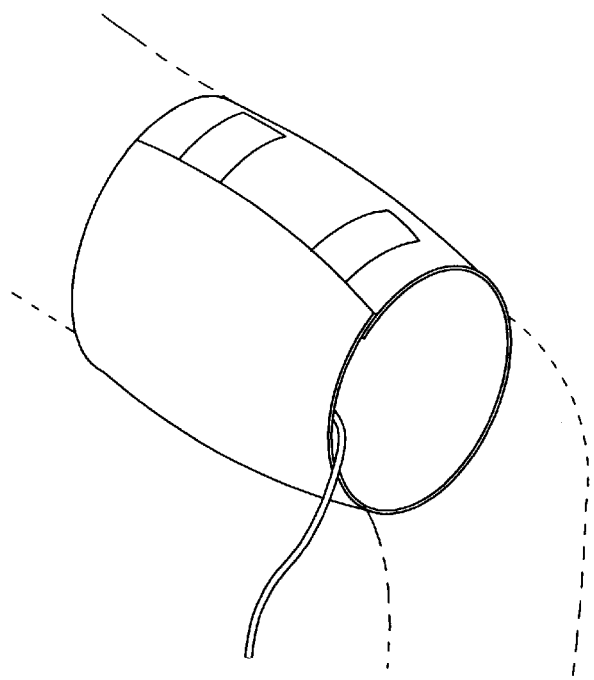

A therapeutic device in accordance with another embodiment of the invention is shown in FIG. 10A. This device generally designated 170 comprises a cloth based matrix 172 and a heating element 174 embedded therein. The heating element, shown herein as a line (which is for ease of illustration only), is a band which is made to track a torturous sinosoidal path throughout the surface of the device. The device comprises fastening straps 176, which as can be inferred from FIG. 103, attach by means of a Velcro™ type attachment to the external surface of the device, forming a therapeutic bandage around an upper leg portion of an individual. The specifications of the electric heating device typically include a power rating of about 120W and an operating voltage of about 6V. The heating element is typically made of stainless steel having a specific resistivity $\rho$ of about 0.75 Ohm-mm$^2$/m, a total length l of 1 m, a width b of about 16 mm and a thickness $\delta$ of about 0.1 mm. The output temperature of the heating element is controllable up to a temperature of about 50° C. by changing the output voltage.

Figure 11:
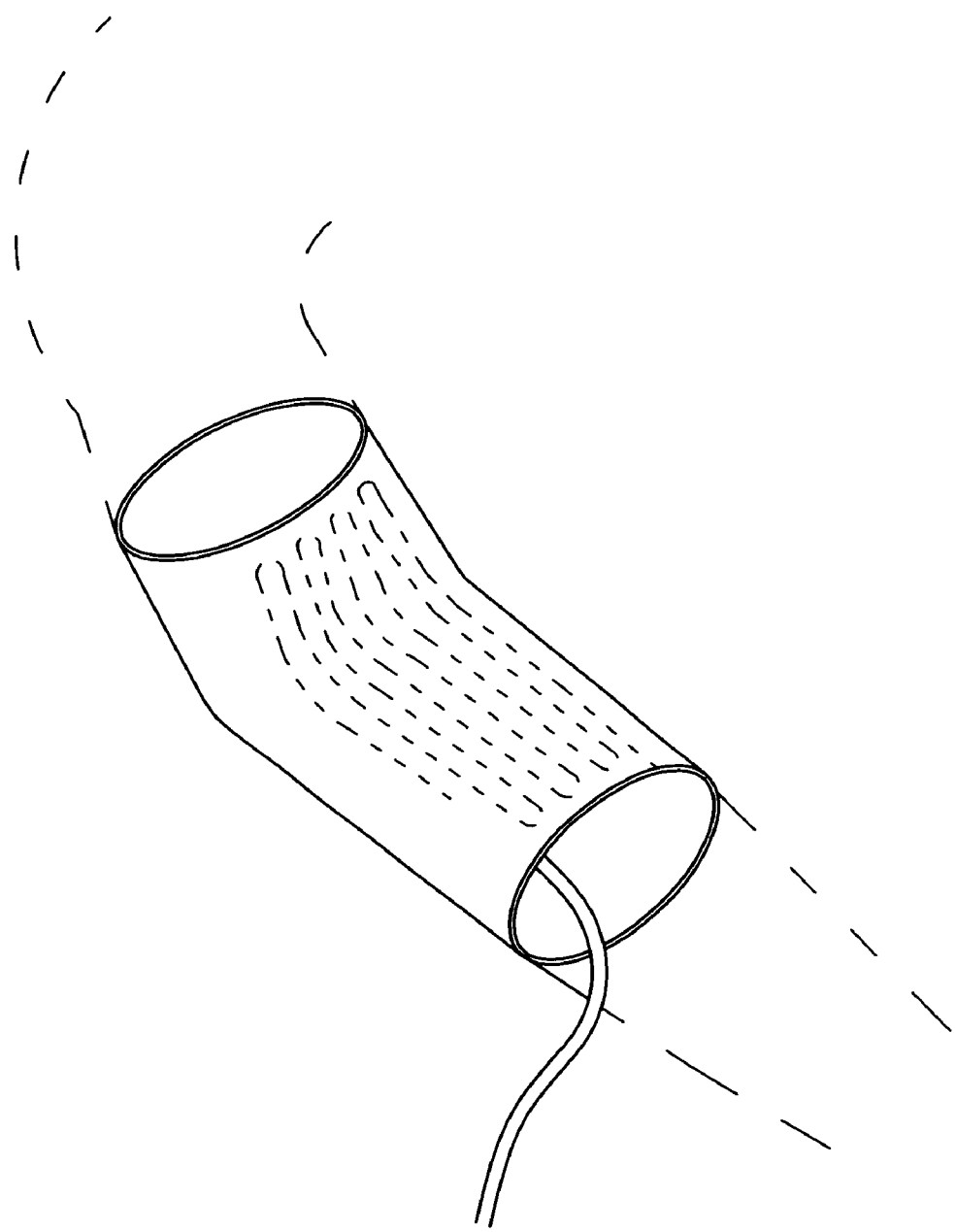
FIG. 11 shows the embodiment of a therapeutic device for heating an individual's elbow region.
Figure 12A:
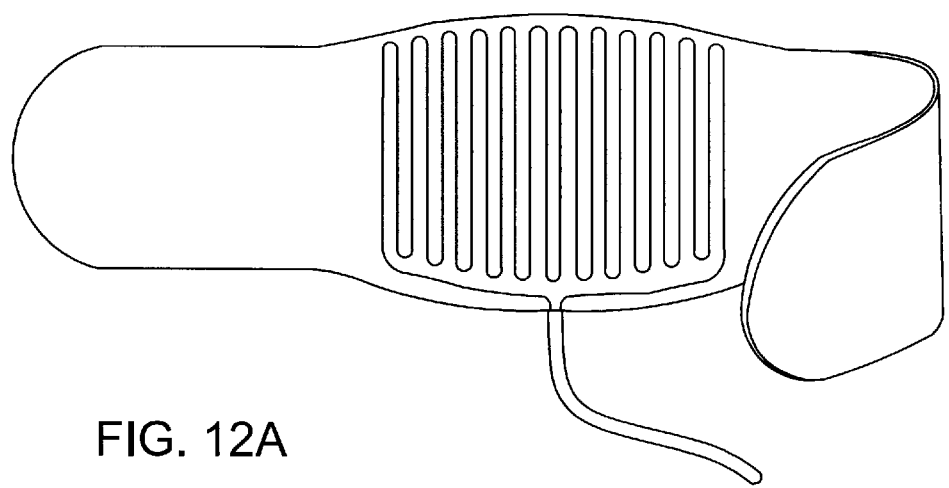
Figure 12B:
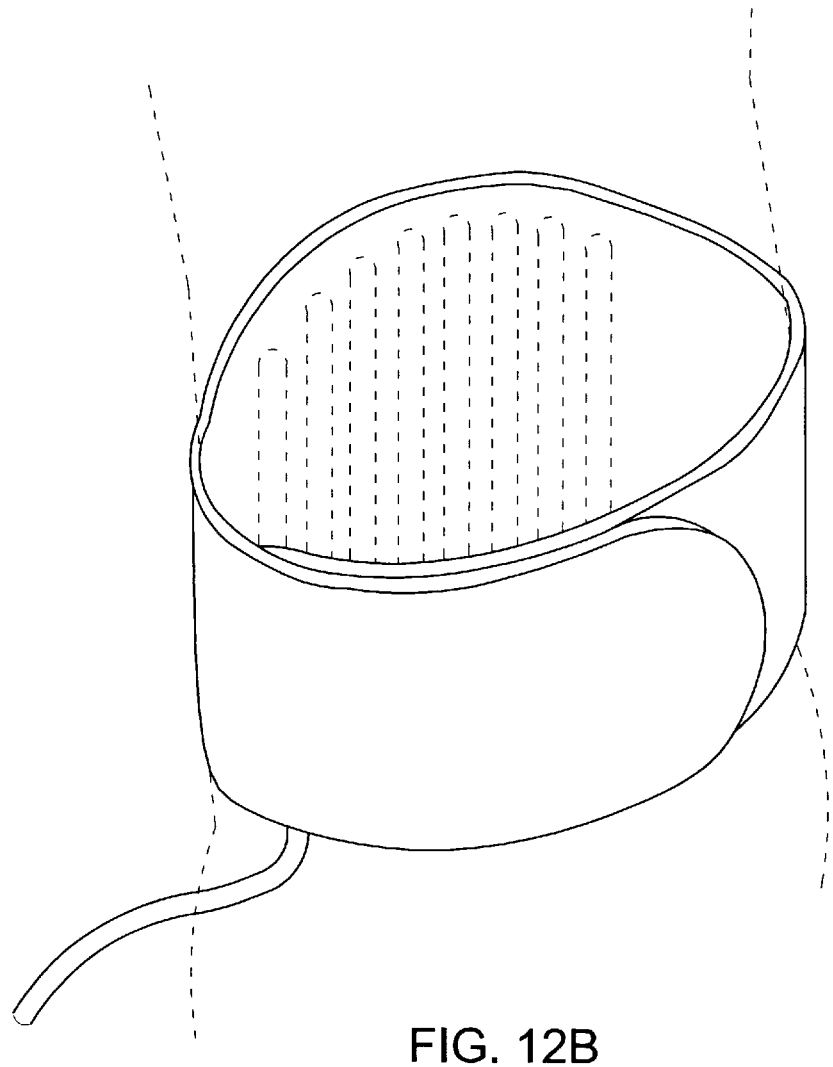
Figure 13:
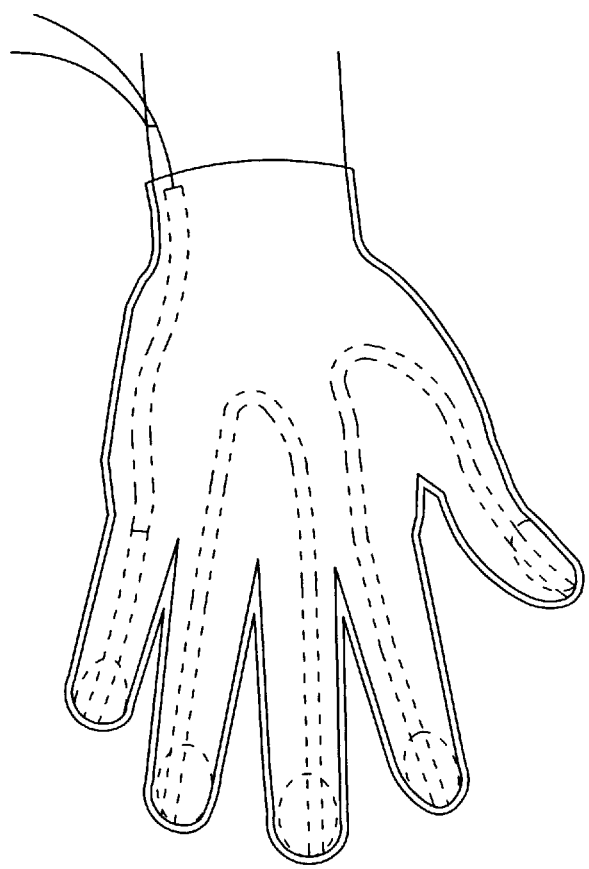
FIGS. 13 and 14 show other embodiments of therapeutic devices of the invention.
Figure 14:
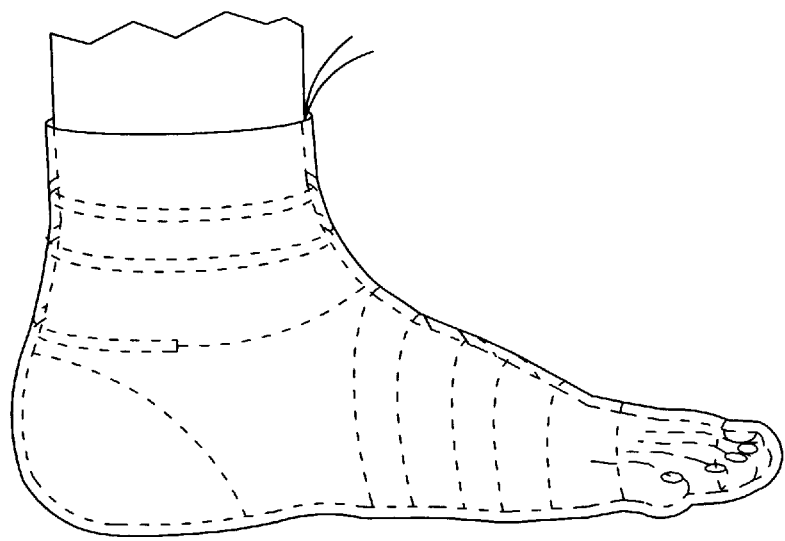

Other therapeutic devices in accordance with the invention are shown in FIGS. 11–15. The device in FIG. 11 is intended for heating an elbow, that shown in FIG. 12 is for heating an individual's back and those in FIGS. 13 and 14 are for heating the hand or a foot, respectively. The device in accordance with the embodiment of FIGS. 13 and 14 can also be designed for use by individuals exposed to extreme cold, such as soldiers, mountain climbers, skiers, etc.

Figure 15:
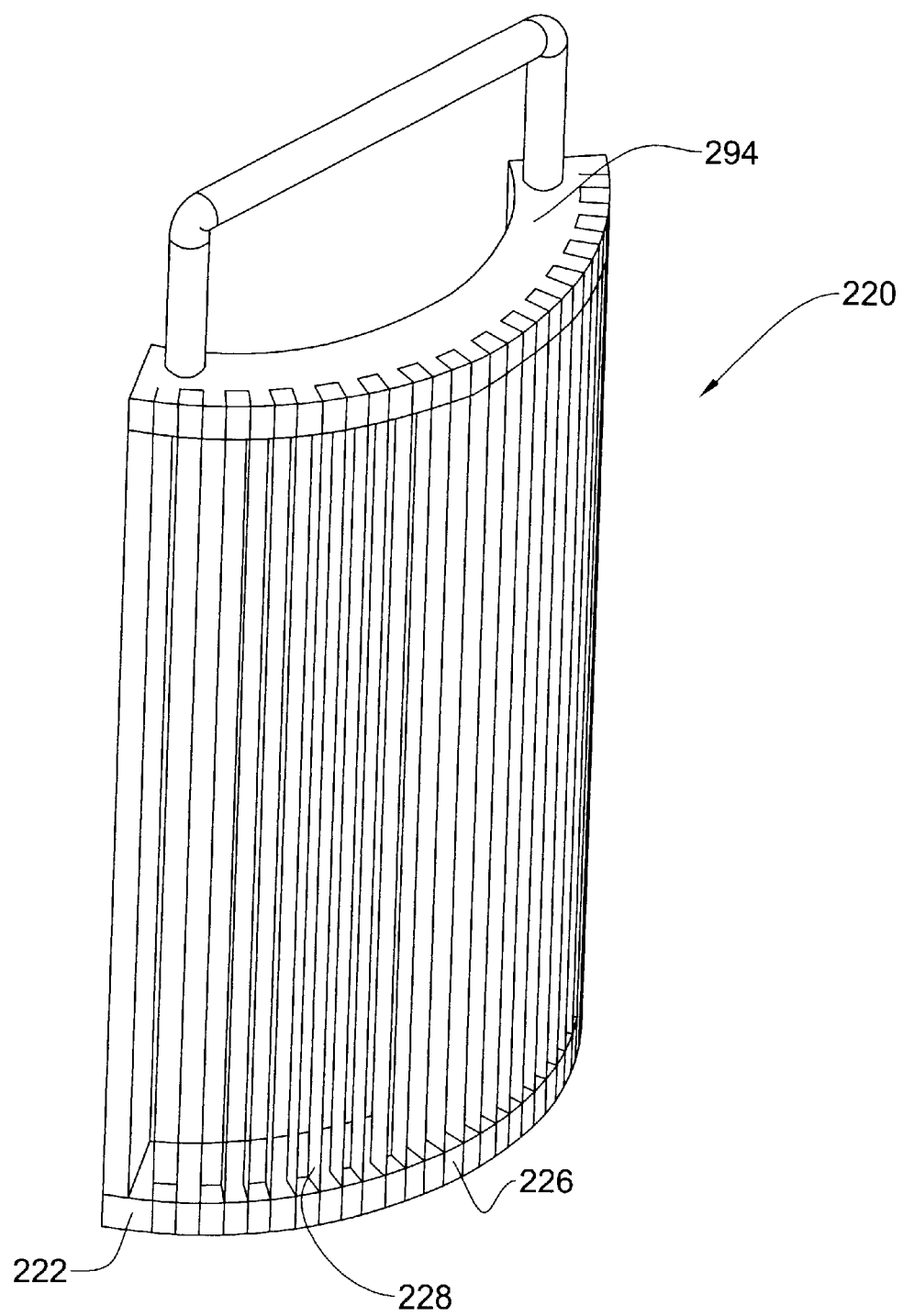
FIG. 15 shows a perspective view of a device for heating a body of air by convection.

Reference is now made to FIG. 15 which shows another embodiment of a domestic heating appliance of the invention, which achieves heating by air convection. The device generally designed 220 of this embodiment consists of a frame 222 which has upper and lower frame sections 224 and 226, respectively, which have a crescent-like shape. The heating device comprises a heating element 228 which is an elongated band which criss-crosses between the upper and the lower frame sections 224 and 226 to form a grill-like structure. The ends of the heating element are connected to an electric power source, typically a low voltage source within the range of 6–24 volts (not shown). A unique feature of this device is that it is lightweight and portable. The heating element 228 may typically have a working temperature within the range of 60–80° C.

Figure 16A:
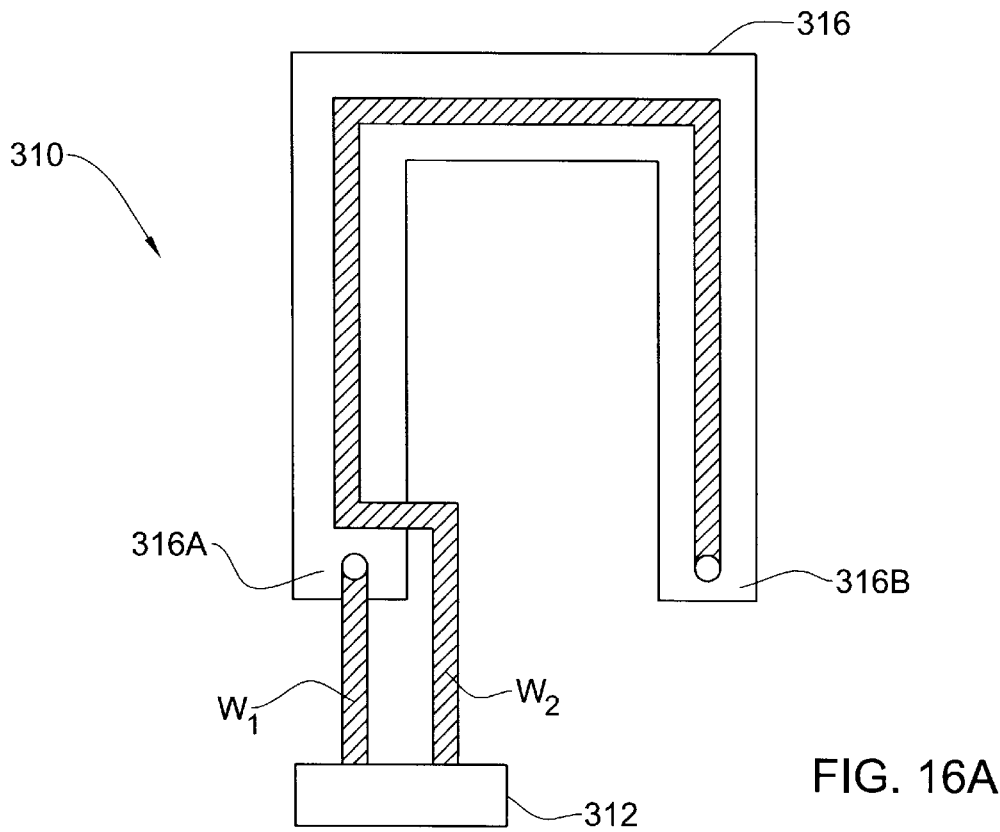
FIGS. 16A and 16B illustrate some more features of the present invention, showing two possible examples of electrical connection between a power source and a heating element.
Figure 16B:
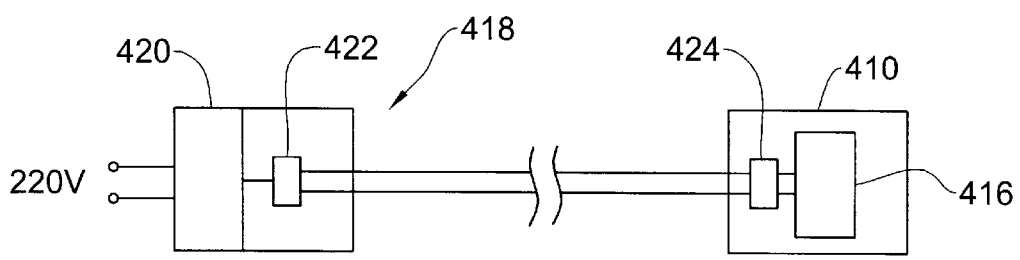

Turning now to FIGS. 16A–16B, there are shown three possible examples of electrical connection between a power source and a heating element.

In the example of 16A, a heating device 310 is shown comprising a heating element 316 connected to a power source 312 through wires $W_1$ and $W_2$. The design of electrical connection is aimed at solving the above-indicated problem of the undesirable existence of an electro-magnetic field produced by the heating element 316 in its vicinity (due to the substantially large area of the element 316 and relatively high electric currents passing therethrough).

As shown, the heating element 316 is a band having two output ends 316A and 316B. The above problem is solved by a specific accommodation of wires $W_1$ and $W_2$ connecting the heating band 316 to the power source 312. Wire $W_1$ is connected directly to one of the output ends of the heating band, i.e., 316A, while wire $W_2$ passes along the entire circuit of the band (substantially symmetrical to the band along its longitudinal axis) and is connected to the other output end 316B.

Figure 16C:
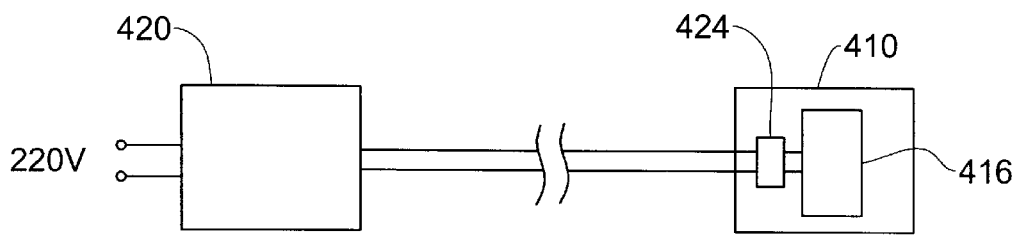

FIGS. 16B and 16C exemplify such applications of a heating device 410, where in order to obtaining low-gradient heating, its heating element 416 should operate with substantially high electric currents and consequently substantially low voltages. A power source utilizes a step-down transformer assembly 418 connected to a power network. As indicated above, at the frequencies of the existing power networks (i.e., 50 Hz and 60 Hz), the weight and dimensions of a step-down transformer are significantly high, which sometimes makes the use of the transformer inefficient.

In the example of FIG. 16B, the operating voltage of the heating element is about IV. The assembly 418 comprises an inverter 420 with an input step-down transformer 422 directly coupled to the power network and an output transformer 424, which is mounted inside the heating device 410 being directly coupled to the heating element 416 and connected to the transformer 422 through wires. The inverter 420 and input transformer 422 operate together to increase the working frequency of the transformer 424 from 50 Hz or 60 Hz to about 15–20 kHz, and to provide the voltage supply to the transformer 424 decreased from 220V (or 110V) to about 24V. This enables to operate with thin flexible wires. The transformer 424 decreases the voltage even more, for example to 1V.

The example of FIG. 16C relates to such a high current low voltage application, where the operational voltage of the heating element needs not be reduced below 24V. In this case, the provision of the input transformer 422 can be eliminated, and the inverter 420 can be directly connected through wires to the transformer 424 mounted inside the heating device 410.

It should be noted that in both examples of FIGS. 16B and 16C, the wires connecting the transformer 424 to the heating element 416 could be accommodated similar to that of the example of FIG. 16A.

While the invention has been described with respect to a limited number of embodiments, it will be appreciated that many variations, modifications and other applications of the invention may be made.

What is claimed is:

1. An electrical heating device for heating an object to a required temperature, the heating device being configured to supply a predefined heating power W to said object and comprising a heating element having a substantially rectangular cross section so as to define at least one major outer surface through which heat is dissipated, and a power source for supplying voltage U to the heating element, wherein:

the voltage U supplied to the heating element and physical parameters of the heating element comprising a specific resistivity $\rho$, length l, width b and thickness $\delta$ are selected so as to satisfy the following relations, at a given power supplied to the heating element which is substantially equal to said predefined power W:

$$b \geq k \cdot I \cdot \sqrt{\frac{\rho}{\delta}}$$

$$l \geq k \cdot U \cdot \sqrt{\frac{\delta}{\rho}}$$

wherein I is the electric current passing through the heating element at the given power W and the selected voltage U; $\rho$ is the specific resistivity (Ohm·mm²/m); $\delta$ is the thickness of the heating element in millimeters; k is a correction coefficient providing the units of length and width in meters and millimeters, respectively, and selected such that increase in the value of k results in increase in the surface area of the heating element and decrease in the surface temperature of the heating element;

the heating device thereby providing a desired temperature gradient between the temperature of said at least one major surface of the heating element and said required temperature.

2. The device according to claim 1, wherein said power source comprises a step-down transformer means.

3. The device according to claim 2, wherein said step-down transformer means comprises an inverter assembly, which is interconnected between a power network and the heating element, and comprises an output step-down transformer mounted inside the heating device and coupled to the heating element.

4. The device according to claim 1, wherein two output ends of the heating element are connected to said power source through two wires, respectively, wherein one of the wires is directly coupled to the corresponding end of the heating element, and the other wire on its way to the other end of the heating element passes along the entire length of the heating element.

5. The device according to claim 1, for use in heating air at room temperature to a temperature of 100° C. or more, or to heat a water based medium consisting of at least 50% water at an initial room temperature, to a temperature up to about 50° C., the coefficient k being within the range of 0.2–0.6.

6. The device according to claim 1, for use in heating air at room temperature to a temperature up to about 90° C. or less, wherein the coefficient k is about 0.6.

7. The heating device according to claim 1, wherein the heating element is incorporated in a structural component in a stationary object.

8. A stationary object such as furniture or the like, comprising the heating element of claim 1 as an added component attached to or embedded with said object.

9. The device according to claim 1, used for food heating, wherein the heating element is in the form of a flat metal body which is either in contact with the food or which is in proximity with the food without any object between it and the food, said metal body being connected to a power source for passing heating electric current therethrough.

10. The device according to claim 9, for heating of liquid food, comprising a metal vessel for holding the food having metal walls serving as the heating elements, and comprising a power source for passing low voltage, high power electric current therethrough, thereby heating the liquid food contained therein.

11. The device according to claim 9, for heating solid food items, in which the solid food items are placed in direct contact with a metal plate, said metal plate serving also as the heating element and being connected to an electric power source for passing a heating electric current therethrough.

12. The device according to claim 9, for heating food by heat irradiation onto the food, comprising a food-containing enclosure having one or more metal walls, at least one of said metal walls serving as the heating element to heat said enclosure and being connected to a power source for passing a heating electric current therethrough.

13. The device according to claim 1, to be worn or held on a body part for heating of that body part, comprising a matrix containing said heating element.

14. The device according to claim 13, wherein said matrix is a cloth or a cloth based matrix.

15. The device according to claim 13, comprising a liquid or gel containing enclosure having fiber walls with the heating elements contained therein.

16. A method for designing an electrical heating device including a heating element and a power source for supplying voltage U to the heating element, for use in a predetermined application consisting of heating a certain object to a required temperature, the method providing for an as low as desired temperature gradient between an operating temperature of an outer surface of the heating element through which heat is dissipated and said required temperature of the heated object, and comprising:

(a) in accordance with the requirements for said as low as desired temperature gradient, defining parameters comprising a power rating W to be supplied to the heating element to dissipate heat through the surface of the heating element, said power being substantially equal to power required for heating said object; a heat dissipating surface area of the heating element; and the operating temperature of said surface at which said heating power is dissipated therethrough;

(b) at the given power rating W, selecting such physical parameters of the heating element as specific resistivity of the heating element material and dimensions of the heating element, and selecting an operating voltage to be supplied to the heating element, to satisfy the following relations:

$$b \geq k \cdot I \cdot \sqrt{\frac{\rho}{\delta}}$$

$$l \geq k \cdot U \cdot \sqrt{\frac{\delta}{\rho}}$$

wherein I is the electric current passing through the heating element at the given power W and the selected voltage U; $\rho$ is the specific resistivity (Ohm·mm$^2$/m); l is the length of the heating element in meters; b is the width of the heating element in millimeters; $\delta$ is the thickness of the heating element in millimeters; k is a correction coefficient providing the units of length and width in meters and millimeters, respectively, and selected such that increase in the value of k results in increase in the surface area of the heating element and decrease in the surface temperature of the heating element.

17. A heating device for heating an object to a required temperature, the heating device comprising a heating element, and a power source including a step-down transformer means and operating for supplying voltage to the heating element, wherein:

the voltage U to be supplied to the heating element is selected in accordance a predetermined application of the heating device;

the heating element is made of a selected electric conductive material of a specific resistivity $\rho$, is substantially flat, and has a substantially rectangular cross section, so as to define at least one major outer surface through which a given heating power required for heating said object to said required temperature is dissipated, length l, width b and thickness $\delta$ of the heating element being selected such as to satisfy the following relations:

$$b \geq k \cdot I \cdot \sqrt{\frac{\rho}{\delta}}$$

$$l \geq k \cdot U \cdot \sqrt{\frac{\delta}{\rho}}$$

wherein I is the electric current passing through the heating element; $\rho$ is the specific resistivity (Ohm·mm$^2$/m); $\delta$ is the thickness of the heating element in millimeters; k is a correction coefficient providing the units of length and width in meters and millimeters, respectively, and selected such that increase in the value of k results in increase in the surface area of the heating element and decrease in the surface temperature of the heating element;

the heating device thereby providing a desired temperature gradient between said at least one major surface of the heating element and said required temperature.

* * * * *